(12) United States Patent
Nizio et al.

(10) Patent No.: US 7,470,439 B1
(45) Date of Patent: Dec. 30, 2008

(54) CHICKEN FEED COMPOSITION AND METHOD OF FEEDING CHICKENS FOR PROMOTING HEALTH OR REJUVENATING EGG PRODUCTION

(75) Inventors: John D. Nizio, Valdosta, GA (US); Nicholas M. Dale, Athens, GA (US)

(73) Assignee: South Georgia Pecan Company, Valdosta, GA (US)

( * ) Notice: Subject to any disclaimer, the term of this patent is extended or adjusted under 35 U.S.C. 154(b) by 0 days.

(21) Appl. No.: 11/170,777

(22) Filed: Jun. 29, 2005

Related U.S. Application Data

(60) Provisional application No. 60/583,920, filed on Jun. 29, 2004.

(51) Int. Cl.
  *A61K 36/00* (2006.01)
  *A61K 36/48* (2006.01)
  *A61K 36/899* (2006.01)

(52) U.S. Cl. .................. 424/725; 424/757; 424/750

(58) Field of Classification Search .............. None
See application file for complete search history.

(56) References Cited

U.S. PATENT DOCUMENTS

| | | | | |
|---|---|---|---|---|
| 2,485,669 | A * | 10/1949 | Sondern | 514/720 |
| 4,098,765 | A * | 7/1978 | Kays et al. | 528/1 |
| 5,629,038 | A * | 5/1997 | Kalmbach | 426/72 |
| 6,511,698 | B1 * | 1/2003 | Kloubec | 426/623 |

FOREIGN PATENT DOCUMENTS

WO   WO 2004/030632 A2 *   4/2004

OTHER PUBLICATIONS

1986. Ramirez et al. Influence of Pecan Shells and Hulls as a Roughage Source on Milk Production, Rumen Fermentation, and Digestion in Ruminants. J. Dairy Sci. 69: pp. 1355-1365.*
1925. Salmon et al. Vitamins A and B in the Pecan Nut. Journal of Home Economics. 43. pp. 129-135.*
Beuchat et al. *Salmonella* Survival on Pecans as Influenced by Processing and Storage Conditions. Applied Microbiology. Jun. 1975. p. 795-801.*
Kirby, Linda K. et al., "The Effect of Seed Coat Color of Hybrid Sorghum Grain on the Ability of Chicks to Digest Dry Matter and Amino Acids and to Utilize Energy," Nutrition Reports International, Apr. 1983, pp. 831-836, vol. 27, No. 4, Elsevier, Inc., St. Louis, MO.
Flores, M.P. et al., "Effect of Tannins on Starch Digestibility and TMEn of Triticale and Semipurified Starches from Triticale and Field Beans," British Poultry Science, 1994, pp. 281-286, vol. 35, Taylor & Francis, Abingdon, UK.
Longstaff, Margaret, et al., "The inhibitory effects of hull polysaccharides and tannins of field beans (*Vicia faba* L.) on the digestion of amino acids, starch and lipid and on digestive enzyme activities in young chicks," British Journal of Nutrition, 1991, pp. 199-216, vol. 65, CABI Publishing, Wallingford, UK.
Tamir, Musha et al. "Inhibition of Digestive Enzymes by Condensed Tannins from Green and Ripe Carobs," Journal of the Science of Food and Agriculture, 1969, pp. 199-202, vol. 20, Society of Chemical Industry, London, UK.
Mitaru, Barnabas N. et al., "The Binding of Dietary Protein by Sorghum Tannins in the Digestive Tract of Pigs," Journal of Nutrition, 1984, pp. 1541-2402, vol. 114, Nos. 9-12, American Institute of Nutrition, Bethesda, MD.
Kays, S. et al.; Analysis of Physical and Chemical Parameters of the Shell of Pecan Genotypes in Reference to the Production of Phenolic Plastics and Resins; HortScience, vol. 17(6), Dec. 1982.

* cited by examiner

*Primary Examiner*—Christopher R. Tate
*Assistant Examiner*—Melenie McCormick
(74) *Attorney, Agent, or Firm*—Smith, Gambrell & Russell

(57) ABSTRACT

A chicken feed composition to promote health or rejuvenate egg production comprising pecan byproduct meal, and a method of feeding chickens to promote health or rejuvenate egg production using the feed composition. Addition of pecan byproduct meal to the feed effectively reduces calorie consumption, body weight, and egg production as desired for the rejuvenation of laying chickens, without resorting to the objectionable practice of extended feed withdrawal. Further, addition of pecan byproduct meal to the feed may positively affect the health of hens in the same manner as conventional fibrous feedstuffs.

19 Claims, 13 Drawing Sheets

FEED INTAKE (Before)

| Tt | | IN 26-Apr Monday | OUT 28-Apr Wed | INTAKE 28-Apr g/hen/day | IN 28-Apr Wed | OUT 30-Apr Friday | INTAKE 30-Apr g/hen/day | | AVG g/hen/day |
|---|---|---|---|---|---|---|---|---|---|
| 1 | 1 | 600.0 | 108.8 | 122.8 | 600.0 | 166.0 | 108.5 | | 115.7 |
| 2 | 2 | 600.0 | 226.0 | 93.5 | 600.0 | 258.2 | 85.5 | | 89.5 |
| 3 | 3 | 600.0 | 427.2 | 43.2 | 600.0 | 345.0 | 63.8 | | 53.5 |
| 4 | 4 | 600.0 | 142.3 | 114.4 | 600.0 | 137.0 | 115.8 | | 115.1 |
| 1 | 5 | 600.0 | 244.0 | 89.0 | 600.0 | 193.7 | 101.6 | | 95.3 |
| 2 | 6 | 600.0 | 324.5 | 68.9 | 600.0 | 267.2 | 83.2 | | 76.0 |
| 3 | 7 | 600.0 | 199.0 | 100.3 | 600.0 | 189.5 | 102.6 | | 101.4 |
| 4 | 8 | 600.0 | 299.4 | 75.2 | 600.0 | 313.5 | 71.6 | | 73.4 |
| 1 | 9 | 600.0 | 194.5 | 101.4 | 600.0 | 139.3 | 115.2 | | 108.3 |
| 2 | 10 | 600.0 | 192.2 | 102.0 | 600.0 | 171.0 | 107.3 | | 104.6 |
| 3 | 11 | 600.0 | 210.0 | 97.5 | 600.0 | 213.0 | 96.8 | | 97.1 |
| 4 | 12 | 600.0 | 193.4 | 101.7 | 600.0 | 195.1 | 101.2 | | 101.4 |
| 1 | 13 | 600.0 | 147.9 | 113.0 | 600.0 | 146.9 | 113.3 | | 113.2 |
| 2 | 14 | 600.0 | 272.0 | 82.0 | 600.0 | 200.5 | 99.9 | | 90.9 |
| 3 | 15 | 600.0 | 439.0 | 80.5 | 600.0 | 380.2 | 109.9 | | 95.2 |
| 4 | 16 | 600.0 | 397.1 | 50.7 | 600.0 | 254.1 | 86.5 | | 68.6 |
| 1 | 17 | 600.0 | 189.1 | 102.7 | 600.0 | 157.5 | 110.6 | | 106.7 |
| 2 | 18 | 600.0 | 234.0 | 91.5 | 600.0 | 207.2 | 98.2 | | 94.9 |
| 3 | 19 | 600.0 | 203.8 | 99.1 | 600.0 | 160.0 | 110.0 | | 104.5 |
| 4 | 20 | 600.0 | 147.0 | 113.3 | 600.0 | 129.2 | 117.7 | | 115.5 |
| 1 | 21 | 600.0 | 122.0 | 119.5 | 600.0 | 157.1 | 110.7 | | 115.1 |
| 2 | 22 | 600.0 | 171.4 | 107.2 | 600.0 | 175.1 | 106.2 | | 106.7 |
| 3 | 23 | 600.0 | 200.0 | 100.0 | 600.0 | 177.3 | 105.7 | | 102.8 |
| 4 | 24 | 600.0 | 179.3 | 105.2 | 600.0 | 156.6 | 110.9 | | 108.0 |
| 1 | 25 | 600.0 | 245.4 | 88.7 | 600.0 | 181.1 | 104.7 | | 96.7 |
| 2 | 26 | 600.0 | 220.0 | 95.0 | 600.0 | 218.3 | 95.4 | | 95.2 |
| 3 | 27 | 600.0 | 173.2 | 106.7 | 600.0 | 214.5 | 96.4 | | 101.5 |
| 4 | 28 | 600.0 | 205.0 | 98.8 | 600.0 | 168.2 | 108.0 | | 103.4 |
| 1 | 29 | 600.0 | 193.7 | 101.6 | 600.0 | 164.4 | 108.9 | | 105.2 |
| 2 | 30 | 600.0 | 161.1 | 109.7 | 600.0 | 128.6 | 117.9 | | 113.8 |
| 3 | 31 | 600.0 | 207.9 | 98.0 | 600.0 | 297.4 | 75.7 | | 86.8 |
| 4 | 32 | 600.0 | 227.0 | 93.3 | 600.0 | 212.7 | 96.8 | | 95.0 |

FEED INTAKE

| | | 30-Apr | 2-May | 2-May | 2-May | 4-May | 4-May | 4-May | 6-May | 6-May | 6-May | 8-May | 8-May | 8-May | 10-May | 10-May | 10-May | 12-May | 12-May | 12-May | 14-May | 14-May |
|---|---|---|---|---|---|---|---|---|---|---|---|---|---|---|---|---|---|---|---|---|---|---|
| | | IN | OUT | INTAKE | IN | OUT | INTAKE | IN | OUT | INTAKE | IN | OUT | INTAKE | IN | OUT | INTAKE | IN | OUT | INTAKE | IN | OUT | INTAKE |
| Tt | | Friday | Sunday | g/hen/day | Sunday | Tuesday | g/hen/day | Tuesday | Thursday | g/hen/day | Thursday | Saturday | g/hen/day | Saturday | Monday | g/hen/day | Monday | Wednesday | g/hen/day | Wednesday | Friday | g/hen/day |
| 1 | 1 | 500.0 | 56.5 | 110.9 | 500.0 | 109.4 | 97.7 | 500.0 | 123.0 | 119.3 | 500.0 | 195.0 | 101.3 | 500.0 | 289.8 | 77.6 | 500.0 | 219.7 | 95.1 | 600.0 | 219.0 | 95.3 |
| 2 | 2 | 500.0 | 377.2 | 30.7 | 500.0 | 273.7 | 56.6 | 500.0 | 226.0 | 68.5 | 500.0 | 138.0 | 90.5 | 500.0 | 101.3 | 99.7 | 550.0 | 69.2 | 120.2 | 550.0 | 79.2 | 117.7 |
| 3 | 3 | 500.0 | 424.2 | 19.0 | 500.0 | 443.5 | 14.1 | 500.0 | 356.0 | 36.0 | 500.0 | 424.0 | 19.0 | 500.0 | 370.7 | 32.3 | 500.0 | 355.2 | 36.2 | 500.0 | 384.0 | 29.0 |
| 4 | 4 | 500.0 | 495.2 | 1.2 | 500.0 | 461.3 | 9.7 | 500.0 | 431.0 | 17.3 | 500.0 | 381.0 | 29.8 | 500.0 | 365.9 | 33.5 | 500.0 | 368.0 | 33.0 | 500.0 | 389.0 | 27.8 |
| 1 | 5 | 500.0 | 86.0 | 103.5 | 500.0 | 125.3 | 93.7 | 500.0 | 182.0 | 104.5 | 500.0 | 167.0 | 108.3 | 600.0 | 225.1 | 93.7 | 600.0 | 181.5 | 104.6 | 600.0 | 209.3 | 97.7 |
| 2 | 6 | 500.0 | 338.1 | 40.5 | 500.0 | 161.0 | 84.8 | 500.0 | 113.0 | 96.8 | 500.0 | 100.0 | 100.0 | 500.0 | 104.1 | 99.0 | 550.0 | 125.0 | 106.3 | 550.0 | 157.2 | 98.2 |
| 3 | 7 | 500.0 | 473.9 | 6.5 | 500.0 | 437.8 | 15.6 | 500.0 | 357.0 | 35.8 | 500.0 | 230.0 | 67.5 | 500.0 | 249.3 | 62.7 | 500.0 | 262.9 | 59.3 | 500.0 | 276.3 | 55.9 |
| 4 | 8 | 500.0 | 476.8 | 5.8 | 500.0 | 423.2 | 19.2 | 500.0 | 373.0 | 31.8 | 500.0 | 333.0 | 41.8 | 500.0 | 318.9 | 45.3 | 500.0 | 337.3 | 40.7 | 500.0 | 351.3 | 37.2 |
| 1 | 9 | 500.0 | 99.5 | 100.1 | 500.0 | 119.7 | 95.1 | 500.0 | 174.0 | 106.5 | 600.0 | 130.0 | 117.5 | 600.0 | 167.5 | 108.1 | 600.0 | 151.8 | 112.1 | 600.0 | 161.0 | 109.8 |
| 2 | 10 | 500.0 | 307.1 | 48.2 | 500.0 | 309.6 | 47.6 | 500.0 | 159.0 | 85.3 | 500.0 | 138.0 | 90.5 | 550.0 | 67.3 | 108.2 | 550.0 | 45.8 | 126.1 | 550.0 | 53.5 | 124.1 |
| 3 | 11 | 500.0 | 381.1 | 29.7 | 500.0 | 324.7 | 43.8 | 500.0 | 294.0 | 51.5 | 500.0 | 243.0 | 64.3 | 500.0 | 237.1 | 65.7 | 500.0 | 312.6 | 46.9 | 500.0 | 328.1 | 43.0 |
| 4 | 12 | 500.0 | 491.6 | 2.1 | 500.0 | 412.9 | 21.8 | 500.0 | 321.0 | 44.8 | 500.0 | 344.0 | 39.0 | 500.0 | 355.2 | 36.2 | 500.0 | 317.1 | 45.7 | 500.0 | 311.4 | 47.2 |
| 1 | 13 | 500.0 | 81.0 | 104.8 | 500.0 | 101.8 | 99.6 | 500.0 | 173.0 | 106.8 | 600.0 | 249.0 | 87.8 | 600.0 | 274.9 | 81.3 | 600.0 | 213.3 | 96.7 | 600.0 | 240.7 | 89.8 |
| 2 | 14 | 500.0 | 218.8 | 70.3 | 500.0 | 162.9 | 84.3 | 500.0 | 141.0 | 89.8 | 500.0 | 170.0 | 82.5 | 500.0 | 148.9 | 87.8 | 550.0 | 91.9 | 114.5 | 550.0 | 98.2 | 113.0 |
| 3 | 15 | 500.0 | 496.5 | 1.8 | 500.0 | 467.3 | 16.4 | 500.0 | 410.0 | 45.0 | 500.0 | 379.0 | 60.5 | 500.0 | 400.5 | 49.8 | 500.0 | 352.3 | 73.9 | 500.0 | 370.0 | 65.0 |
| 4 | 16 | 500.0 | 487.4 | 3.2 | 500.0 | 438.7 | 15.3 | 500.0 | 403.0 | 24.3 | 500.0 | 339.0 | 40.3 | 500.0 | 375.9 | 31.0 | 500.0 | 335.0 | 41.2 | 500.0 | 356.2 | 36.0 |
| 1 | 17 | 500.0 | 65.9 | 108.5 | 500.0 | 145.7 | 88.6 | 500.0 | 272.0 | 82.0 | 500.0 | 210.0 | 97.5 | 500.0 | 251.6 | 87.1 | 600.0 | 170.2 | 107.5 | 600.0 | 213.2 | 96.7 |
| 2 | 18 | 500.0 | 191.9 | 77.0 | 500.0 | 153.8 | 86.6 | 500.0 | 75.0 | 106.3 | 500.0 | 57.0 | 110.8 | 500.0 | 57.0 | 110.8 | 550.0 | 18.3 | 132.9 | 550.0 | 53.0 | 124.3 |
| 3 | 19 | 500.0 | 440.4 | 14.9 | 500.0 | 256.6 | 60.9 | 500.0 | 317.0 | 45.8 | 500.0 | 318.0 | 45.5 | 500.0 | 162.2 | 84.5 | 500.0 | 166.1 | 83.5 | 500.0 | 121.2 | 94.7 |
| 4 | 20 | 500.0 | 482.5 | 4.4 | 500.0 | 429.2 | 17.7 | 500.0 | 139.0 | 96.3 | 500.0 | 193.0 | 101.8 | 500.0 | 326.9 | 43.3 | 500.0 | 289.9 | 52.5 | 500.0 | 306.4 | 48.4 |
| 1 | 21 | 500.0 | 67.1 | 108.2 | 500.0 | 83.8 | 104.1 | 500.0 | 154.0 | 86.5 | 500.0 | 117.0 | 95.8 | 500.0 | 283.2 | 79.2 | 600.0 | 116.4 | 120.9 | 600.0 | 179.9 | 105.0 |
| 2 | 22 | 500.0 | 380.1 | 30.0 | 500.0 | 223.0 | 69.3 | 500.0 | 154.0 | 86.5 | 500.0 | 117.0 | 95.8 | 500.0 | 116.9 | 95.8 | 550.0 | 79.0 | 117.8 | 550.0 | 133.0 | 104.3 |
| 3 | 23 | 500.0 | 345.3 | 38.7 | 500.0 | 257.6 | 60.6 | 500.0 | 251.0 | 62.3 | 500.0 | 221.0 | 69.8 | 500.0 | 243.0 | 64.3 | 500.0 | 57.4 | 110.7 | 500.0 | 218.3 | 70.4 |
| 4 | 24 | 500.0 | 451.7 | 12.1 | 500.0 | 392.5 | 26.9 | 500.0 | 308.0 | 48.0 | 500.0 | 249.0 | 62.8 | 500.0 | 310.8 | 47.3 | 500.0 | 252.9 | 61.8 | 500.0 | 251.0 | 62.3 |
| 1 | 25 | 500.0 | 118.9 | 95.3 | 500.0 | 119.6 | 95.1 | 500.0 | 145.0 | 113.8 | 500.0 | 145.0 | 113.8 | 500.0 | 177.4 | 105.7 | 600.0 | 78.5 | 130.4 | 600.0 | 149.7 | 112.6 |
| 2 | 26 | 500.0 | 418.9 | 20.3 | 500.0 | 318.4 | 45.4 | 500.0 | 173.0 | 81.8 | 500.0 | 135.0 | 91.3 | 500.0 | 136.4 | 90.9 | 550.0 | 173.4 | 94.2 | 550.0 | 147.2 | 100.7 |
| 3 | 27 | 500.0 | 444.6 | 13.9 | 500.0 | 310.4 | 47.4 | 500.0 | 117.0 | 95.8 | 500.0 | 154.0 | 86.5 | 500.0 | 229.5 | 67.6 | 500.0 | 164.2 | 84.0 | 500.0 | 184.0 | 79.0 |
| 4 | 28 | 500.0 | 476.8 | 5.8 | 500.0 | 398.0 | 25.5 | 500.0 | 368.0 | 33.0 | 500.0 | 316.0 | 46.0 | 500.0 | 267.6 | 58.1 | 500.0 | 254.0 | 61.5 | 500.0 | 305.8 | 48.6 |
| 1 | 29 | 500.0 | 89.1 | 102.7 | 500.0 | 75.0 | 106.3 | 500.0 | 156.0 | 111.0 | 500.0 | 127.0 | 118.3 | 500.0 | 187.1 | 103.2 | 600.0 | 102.3 | 124.4 | 600.0 | 184.1 | 104.0 |
| 2 | 30 | 500.0 | 305.9 | 48.5 | 500.0 | 165.4 | 83.7 | 500.0 | 105.0 | 98.8 | 500.0 | 129.0 | 92.8 | 500.0 | 59.0 | 110.3 | 550.0 | 55.1 | 123.7 | 550.0 | 101.3 | 112.2 |
| 3 | 31 | 500.0 | 427.2 | 18.2 | 500.0 | 376.8 | 30.8 | 500.0 | 382.0 | 29.5 | 500.0 | 368.0 | 33.0 | 500.0 | 390.1 | 27.5 | 500.0 | 380.4 | 29.9 | 500.0 | 376.0 | 31.0 |
| 4 | 32 | 500.0 | 495.3 | 1.2 | 500.0 | 408.9 | 22.8 | 500.0 | 402.0 | 24.5 | 500.0 | 321.0 | 44.8 | 500.0 | 327.7 | 43.1 | 500.0 | 327.6 | 43.1 | 500.0 | 363.3 | 34.2 |

FIG. 2

| Body Weight (g) | | | | | | | | |
|---|---|---|---|---|---|---|---|---|
| Start | | | Day 7 | | | Day 14 | | |
| Tt | Bird 1 | Bird 2 | Avg. | Bird 1 | Bird 2 | Avg. | Bird 1 | Bird 2 | Avg. |
| 1 | 1980 | 1855 | 1917.5 | 1867 | 1962 | 1914.5 | 1805 | 1907 | 1856.0 |
| 2 | 1925 | 1838 | 1881.5 | 1540 | 1710 | 1625.0 | 1567 | 1724 | 1645.5 |
| 3 | 1895 | 1888 | 1891.5 | 1370 | 1650 | 1510.0 | 1503 | 1273 | 1388.0 |
| 4 | 2190 | 2075 | 2132.5 | 1574 | 1852 | 1713.0 | 1817 | 1457 | 1637.0 |
| 1 | 1880 | 1870 | 1875.0 | 1790 | 1817 | 1803.5 | 1758 | 1867 | 1812.5 |
| 2 | 1970 | 1950 | 1960.0 | 1796 | 1643 | 1719.5 | 1714 | 1625 | 1669.5 |
| 3 | 1750 | 1855 | 1802.5 | 1517 | 1396 | 1456.5 | 1589 | 1427 | 1508.0 |
| 4 | 1780 | 1731 | 1755.5 | 1338 | 1417 | 1377.5 | 1373 | 1317 | 1345.0 |
| 1 | 1775 | 1870 | 1822.5 | 1666 | 1910 | 1788.0 | 1905 | 1648 | 1776.5 |
| 2 | 1704 | 1980 | 1842.0 | 1492 | 1730 | 1611.0 | 1707 | 1524 | 1615.5 |
| 3 | 1866 | 2045 | 1955.5 | 1715 | 1577 | 1646.0 | 1550 | 1665 | 1607.5 |
| 4 | 1945 | 2090 | 2017.5 | 1670 | 1608 | 1639.0 | 1510 | 1529 | 1519.5 |
| 1 | 1700 | 1720 | 1710.0 | 1594 | 1678 | 1636.0 | 1690 | 1628 | 1659.0 |
| 2 | 2065 | 2145 | 2105.0 | 1789 | 1819 | 1804.0 | 1828 | 1828 | 1828.0 |
| 3 | 1920 | | 1920.0 | 1804 | | 1804.0 | 1743 | | 1743.0 |
| 4 | 1810 | 1750 | 1780.0 | 1426 | 1390 | 1408.0 | 1303 | 1331 | 1317.0 |
| 1 | 1875 | 2085 | 1980.0 | 1917 | 1765 | 1841.0 | 1885 | 1764 | 1824.5 |
| 2 | 1934 | 1770 | 1852.0 | 1655 | 1805 | 1730.0 | 1617 | 1687 | 1652.0 |
| 3 | 2032 | 1980 | 2006.0 | 1569 | 1875 | 1722.0 | 1602 | 1804 | 1703.0 |
| 4 | 1740 | 1985 | 1862.5 | 1373 | 1679 | 1526.0 | 1324 | 1610 | 1467.0 |
| 1 | 2090 | 1945 | 2017.5 | 2078 | 1882 | 1980.0 | 1973 | 1877 | 1925.0 |
| 2 | 1960 | 1780 | 1870.0 | 1561 | 1746 | 1653.5 | 1586 | 1694 | 1640.0 |
| 3 | 2070 | 1815 | 1942.5 | 1564 | 1763 | 1663.5 | 1647 | 1606 | 1626.5 |
| 4 | 1733 | 1730 | 1731.5 | 1383 | 1436 | 1409.5 | 1377 | 1361 | 1369.0 |
| 1 | 2127 | 2055 | 2091.0 | 1914 | 2101 | 2007.5 | 2130 | 1881 | 2005.5 |
| 2 | 1983 | 1930 | 1956.5 | 1625 | 1756 | 1690.5 | 1473 | 1950 | 1711.5 |
| 3 | 1718 | 1805 | 1761.5 | 1619 | 1414 | 1516.5 | 1339 | 1501 | 1420.0 |
| 4 | 2075 | 2194 | 2134.5 | 1749 | 1715 | 1732.0 | 1698 | 1678 | 1688.0 |
| 1 | 2010 | 1765 | 1887.5 | 1704 | 2029 | 1866.5 | 1999 | 1647 | 1823.0 |
| 2 | 1830 | 1757 | 1793.5 | 1583 | 1666 | 1624.5 | 1648 | 1513 | 1580.5 |
| 3 | 1970 | 1975 | 1972.5 | 1591 | 1548 | 1569.5 | 1430 | 1550 | 1490.0 |
| 4 | 1950 | 1743 | 1846.5 | 1347 | 1516 | 1431.5 | 1277 | 1465 | 1371.0 |
| AVG. = | | | 1908.6 | | | 1669.4 | | | 1632.0 |

FIG. 4

EGG PRODUCTION (Before)

| Tt | | 24-Apr Saturday | 25-Apr Sunday | 26-Apr Monday | 27-Apr Tuesday | 28-Apr Wed | 29-Apr Thursday | 30-Apr Friday | Total |
|---|---|---|---|---|---|---|---|---|---|
| 1 | 1 | 2 | 1 | 2 | 1 | 2 | 2 | 2 | 12 |
| 2 | 2 | 1 | 2 | 2 | 1 | 1 | 2 | 2 | 11 |
| 3 | 3 | 2 | 1 | 2 | 2 | 1 | 2 | 2 | 12 |
| 4 | 4 | 2 | 1 | 2 | 2 | 2 | 1 | 1 | 11 |
| 1 | 5 | 2 | 2 | 2 | 1 | 1 | 1 | 2 | 11 |
| 2 | 6 | 2 | 2 | 1 | 1 | 1 | 1 | 2 | 10 |
| 3 | 7 | 1 | 2 | 2 | 1 | 2 | 2 | 2 | 12 |
| 4 | 8 | 2 | 1 | 1 | 0 | 2 | 1 | 1 | 8 |
| 1 | 9 | 2 | 2 | 1 | 0 | 1 | 2 | 2 | 10 |
| 2 | 10 | 1 | 2 | 1 | 1 | 2 | 2 | 1 | 10 |
| 3 | 11 | 1 | 2 | 1 | 1 | 2 | 2 | 2 | 11 |
| 4 | 12 | 2 | 0 | 2 | 0 | 2 | 0 | 2 | 8 |
| 1 | 13 | 2 | 2 | 1 | 1 | 2 | 0 | 2 | 10 |
| 2 | 14 | 2 | 1 | 2 | 1 | 1 | 1 | 2 | 10 |
| 3 | 15 | 1 | 1 | 1 | 1 | 0 | 1 | 2 | 7 |
| 4 | 16 | 1 | 2 | 1 | 0 | 1 | 1 | 1 | 7 |
| 1 | 17 | 2 | 2 | 2 | 1 | 1 | 2 | 2 | 12 |
| 2 | 18 | 1 | 2 | 2 | 1 | 2 | 1 | 2 | 11 |
| 3 | 19 | 2 | 2 | 1 | 1 | 2 | 2 | 2 | 12 |
| 4 | 20 | 2 | 1 | 2 | 1 | 1 | 2 | 2 | 11 |
| 1 | 21 | 1 | 2 | 1 | 0 | 1 | 2 | 2 | 9 |
| 2 | 22 | 2 | 1 | 2 | 2 | 2 | 1 | 2 | 12 |
| 3 | 23 | 1 | 2 | 2 | 2 | 2 | 1 | 2 | 12 |
| 4 | 24 | 2 | 2 | 2 | 2 | 1 | 2 | 2 | 13 |
| 1 | 25 | 1 | 2 | 1 | 0 | 2 | 2 | 2 | 10 |
| 2 | 26 | 1 | 2 | 2 | 1 | 1 | 2 | 3 | 12 |
| 3 | 27 | 2 | 2 | 1 | 2 | 2 | 1 | 1 | 11 |
| 4 | 28 | 2 | 1 | 1 | 0 | 2 | 2 | 2 | 10 |
| 1 | 29 | 1 | 2 | 1 | 0 | 2 | 1 | 2 | 9 |
| 2 | 30 | 1 | 2 | 2 | 0 | 1 | 1 | 2 | 9 |
| 3 | 31 | 2 | 1 | 1 | 0 | 2 | 2 | 2 | 10 |
| 4 | 32 | 2 | 1 | 2 | 1 | 2 | 2 | 2 | 12 |
| Total: | | 51 | 51 | 49 | 28 | 49 | 47 | 60 | 335 |

FIG. 6

EGG PRODUCTION

| Tt | | 1-May Saturday | 2-May Sunday | 3-May Monday | 4-May Tuesday | 5-May Wednesday | 6-May Thursday | 7-May Friday | 8-May Saturday | 9-May Sunday | 10-May Monday | 11-May Tuesday | 12-May Wednesday | 13-May Thursday | 14-May Friday | Total |
|---|---|---|---|---|---|---|---|---|---|---|---|---|---|---|---|---|
| 1 | 1 | 1 | 2 | 2 | 1 | 2 | 2 | 2 | 2 | 2 | 1 | 2 | 2 | 1 | 2 | 24 |
| 2 | 2 | 1 | 1 | 1 | 0 | 1 | 1 | 1 | 0 | 1 | 1 | 0 | 1 | 1 | 0 | 10 |
| 3 | 3 | 1 | 2 | 0 | 0 | 0 | 1 | 0 | 1 | 1 | 0 | 1 | 0 | 1 | 0 | 8 |
| 4 | 4 | 0 | 2 | 1 | 1 | 0 | 0 | 0 | 0 | 0 | 0 | 0 | 0 | 0 | 0 | 4 |
| 1 | 5 | 0 | 2 | 2 | 2 | 2 | 1 | 2 | 2 | 2 | 1 | 1 | 2 | 2 | 1 | 22 |
| 2 | 6 | 0 | 1 | 1 | 0 | 0 | 0 | 0 | 1 | 0 | 1 | 1 | 0 | 1 | 1 | 7 |
| 3 | 7 | 1 | 1 | 0 | 0 | 0 | 0 | 0 | 0 | 0 | 0 | 0 | 0 | 0 | 0 | 2 |
| 4 | 8 | 1 | 0 | 0 | 0 | 1 | 0 | 0 | 0 | 0 | 0 | 0 | 0 | 0 | 0 | 2 |
| 1 | 9 | 0 | 2 | 1 | 1 | 2 | 1 | 2 | 2 | 2 | 1 | 2 | 1 | 2 | 2 | 21 |
| 2 | 10 | 1 | 1 | 2 | 2 | 1 | 0 | 2 | 1 | 1 | 1 | 1 | 0 | 1 | 1 | 15 |
| 3 | 11 | 1 | 2 | 1 | 2 | 0 | 1 | 0 | 0 | 0 | 0 | 0 | 0 | 1 | 1 | 9 |
| 4 | 12 | 1 | 0 | 0 | 0 | 0 | 0 | 0 | 0 | 0 | 1 | 0 | 0 | 0 | 0 | 2 |
| 1 | 13 | 1 | 2 | 2 | 2 | 2 | 1 | 2 | 1 | 1 | 1 | 2 | 2 | 0 | 2 | 21 |
| 2 | 14 | 1 | 2 | 2 | 1 | 1 | 1 | 1 | 0 | 0 | 0 | 0 | 0 | 0 | 0 | 9 |
| 3 | 15 | 0 | 1 | 0 | 0 | 0 | 0 | 0 | 0 | 0 | 0 | 0 | 0 | 0 | 0 | 1 |
| 4 | 16 | 1 | 0 | 0 | 0 | 0 | 0 | 0 | 0 | 0 | 0 | 0 | 0 | 0 | 0 | 1 |
| 1 | 17 | 1 | 2 | 2 | 1 | 1 | 2 | 2 | 2 | 2 | 1 | 2 | 1 | 1 | 2 | 22 |
| 2 | 18 | 0 | 2 | 2 | 0 | 2 | 1 | 1 | 2 | 1 | 1 | 2 | 0 | 2 | 2 | 18 |
| 3 | 19 | 1 | 2 | 0 | 1 | 0 | 1 | 1 | 0 | 0 | 0 | 0 | 1 | 1 | 0 | 8 |
| 4 | 20 | 0 | 1 | 1 | 0 | 0 | 0 | 0 | 0 | 0 | 0 | 0 | 0 | 0 | 0 | 2 |
| 1 | 21 | 2 | 2 | 2 | 2 | 1 | 2 | 1 | 2 | 1 | 1 | 2 | 2 | 2 | 1 | 23 |
| 2 | 22 | 1 | 1 | 1 | 0 | 0 | 0 | 0 | 1 | 1 | 0 | 1 | 1 | 1 | 1 | 9 |
| 3 | 23 | 1 | 2 | 0 | 0 | 2 | 1 | 0 | 0 | 0 | 0 | 0 | 0 | 0 | 0 | 6 |
| 4 | 24 | 1 | 1 | 0 | 0 | 0 | 0 | 0 | 0 | 0 | 0 | 0 | 0 | 0 | 0 | 2 |
| 1 | 25 | 1 | 2 | 1 | 1 | 2 | 2 | 2 | 2 | 1 | 1 | 2 | 2 | 1 | 2 | 22 |
| 2 | 26 | 1 | 2 | 0 | 0 | 0 | 0 | 1 | 0 | 1 | 1 | 1 | 0 | 1 | 0 | 8 |
| 3 | 27 | 1 | 1 | 1 | 1 | 1 | 1 | 0 | 1 | 0 | 1 | 0 | 1 | 1 | 0 | 10 |
| 4 | 28 | 0 | 2 | 0 | 0 | 0 | 0 | 0 | 0 | 0 | 0 | 0 | 0 | 0 | 0 | 2 |
| 1 | 29 | 0 | 3 | 1 | 2 | 2 | 1 | 2 | 2 | 2 | 2 | 2 | 1 | 2 | 2 | 24 |
| 2 | 30 | 0 | 3 | 1 | 2 | 2 | 1 | 2 | 2 | 1 | 1 | 1 | 2 | 1 | 1 | 19 |
| 3 | 31 | 1 | 2 | 1 | 0 | 0 | 0 | 0 | 0 | 0 | 0 | 0 | 0 | 0 | 0 | 4 |
| 4 | 32 | 0 | 2 | 1 | 0 | 1 | 0 | 0 | 0 | 0 | 0 | 0 | 0 | 0 | 0 | 4 |
| Total: | | 22 | 51 | 29 | 22 | 26 | 21 | 24 | 23 | 20 | 17 | 23 | 19 | 23 | 21 | 341 |

|    |    | Body Weight (g) | | | | | | Weight Loss (%) | |
|----|----|-------|-------|------|------|------|------|----|-------|-------|
|    |    | Start | | Day 7 | | Day 14 | | | Day 7 | Day 14 |
| Tt | CAGE | BIRD | CAGE | BIRD | CAGE | BIRD | | % | % |
| 1 | A | 3920 | 1,960 | 3380 | 1,690 | 3402 | 1,701 | 1 | 13.78 | 13.21 |
| 2 | B | 3792 | 1,896 | 3348 | 1,674 | 3338 | 1,669 | 2 | 11.71 | 11.97 |
| 3 | C | 4690 | 2,345 | 3950 | 1,975 | 3940 | 1,970 | 3 | 15.78 | 15.99 |
| 4 | D | 4036 | 2,018 | 3379 | 1,690 | 3345 | 1,673 | 4 | 16.28 | 17.12 |
| 5 | E | 3690 | 1,845 | 2950 | 1,475 | 2891 | 1,446 | 5 | 20.05 | 21.65 |
| 6 | F | 3838 | 1,919 | 2946 | 1,473 | 2644 | 1,322 | 6 | 23.24 | 31.11 |
| 7 | A | 3716 | 1,858 | 2965 | 1,483 | 3158 | 1,579 | 7 | 20.21 | 15.02 |
| 8 | B | 3668 | 1,834 | 3049 | 1,525 | 3080 | 1,540 | 8 | 16.88 | 16.03 |
| 9 | C | 3920 | 1,960 | 3365 | 1,683 | 3290 | 1,645 | 9 | 14.16 | 16.07 |
| 10 | D | 4064 | 2,032 | 3309 | 1,655 | 3288 | 1,644 | 10 | 18.58 | 19.09 |
| 11 | E | 4478 | 2,239 | 3500 | 1,750 | 3368 | 1,684 | 11 | 21.84 | 24.79 |
| 12 | F | 3600 | 1,800 | 2812 | 1,406 | 2568 | 1,284 | 12 | 21.89 | 28.67 |
| 13 | A | 3955 | 1,978 | 3420 | 1,710 | 3356 | 1,678 | 13 | 13.53 | 15.15 |
| 14 | B | 4340 | 2,170 | 3741 | 1,871 | 3740 | 1,870 | 14 | 13.80 | 13.82 |
| 15 | C | 3792 | 1,896 | 3125 | 1,563 | 3102 | 1,551 | 15 | 17.59 | 18.20 |
| 16 | D | 4200 | 2,100 | 3309 | 1,655 | 3342 | 1,671 | 16 | 21.21 | 20.43 |
| 17 | E | 4060 | 2,030 | 3380 | 1,690 | 3240 | 1,620 | 17 | 16.75 | 20.20 |
| 18 | F | 3905 | 1,953 | 3195 | 1,598 | 2999 | 1,500 | 18 | 18.18 | 23.20 |
| 19 | A | 3670 | 1,835 | 3300 | 1,650 | 3224 | 1,612 | 19 | 10.08 | 12.15 |
| 20 | B | 4010 | 2,005 | 3388 | 1,694 | 3400 | 1,700 | 20 | 15.51 | 15.21 |
| 21 | C | 3470 | 1,735 | 2817 | 1,409 | 2872 | 1,436 | 21 | 18.82 | 17.23 |
| 22 | D | 4124 | 2,062 | 3359 | 1,680 | 3131 | 1,566 | 22 | 18.55 | 24.08 |
| 23 | E | 3420 | 1,710 | 2727 | 1,364 | 2638 | 1,319 | 23 | 20.26 | 22.87 |
| 24 | F | 3885 | 1,943 | 3332 | 1,666 | 3185 | 1,593 | 24 | 14.23 | 18.02 |
| 25 | A | 4490 | 2,245 | 3795 | 1,898 | 3608 | 1,804 | 25 | 15.48 | 19.64 |
| 26 | B | 4610 | 2,305 | 3812 | 1,906 | 3695 | 1,848 | 26 | 17.31 | 19.85 |
| 27 | C | 4115 | 2,058 | 3481 | 1,741 | 3502 | 1,751 | 27 | 15.41 | 14.90 |
| 28 | D | 3720 | 1,860 | 3086 | 1,543 | 3070 | 1,535 | 28 | 17.04 | 17.47 |
| 29 | E | 3660 | 1,830 | 2930 | 1,465 | 2926 | 1,463 | 29 | 19.95 | 20.05 |
| 30 | F | 3760 | 1,880 | 3010 | 1,505 | 2842 | 1,421 | 30 | 19.95 | 24.41 |
| 31 | A | 3450 | 1,725 | 2917 | 1,459 | 2912 | 1,456 | 31 | 15.45 | 15.59 |
| 32 | B | 3555 | 1,778 | 3016 | 1,508 | 3109 | 1,555 | 32 | 15.16 | 12.55 |
| 33 | C | 4045 | 2,023 | 3445 | 1,723 | 3524 | 1,762 | 33 | 14.83 | 12.88 |
| 34 | D | 4240 | 2,120 | 3527 | 1,764 | 3538 | 1,769 | 34 | 16.82 | 16.56 |
| 35 | E | 3770 | 1,885 | 2970 | 1,485 | 2840 | 1,420 | 35 | 21.22 | 24.67 |
| 36 | F | 4380 | 2,190 | 3557 | 1,779 | 3187 | 1,594 | 36 | 18.79 | 27.24 |
| 37 | A | 4110 | 2,055 | 3591 | 1,796 | 3600 | 1,800 | 37 | 12.63 | 12.41 |
| 38 | B | 4038 | 2,019 | 3505 | 1,753 | 3380 | 1,690 | 38 | 13.20 | 16.30 |
| 39 | C | 3960 | 1,980 | 3483 | 1,742 | 3276 | 1,638 | 39 | 12.05 | 17.27 |
| 40 | D | 3939 | 1,970 | 3369 | 1,685 | 3290 | 1,645 | 40 | 14.47 | 16.48 |
| 41 | E | 3810 | 1,905 | 3099 | 1,550 | 2930 | 1,465 | 41 | 18.66 | 23.10 |
| 42 | F | 3870 | 1,935 | 3002 | 1,501 | 2755 | 1,378 | 42 | 22.43 | 28.81 |
| 43 | A | 3680 | 1,840 | 3197 | 1,599 | 3158 | 1,579 | 43 | 13.13 | 14.18 |
| 44 | B | 4085 | 2,043 | 3552 | 1,776 | 3424 | 1,712 | 44 | 13.05 | 16.18 |
| 45 | C | 4190 | 2,095 | 3643 | 1,822 | 3528 | 1,764 | 45 | 13.05 | 15.80 |
| 46 | D | 4650 | 2,325 | 3748 | 1,874 | 3568 | 1,784 | 46 | 19.40 | 23.27 |
| 47 | E | 4590 | 2,295 | 3255 | 1,628 | 3060 | 1,530 | 47 | 29.08 | 33.33 |
| 48 | F | 4770 | 2,385 | 3309 | 1,655 | 3157 | 1,579 | 48 | 30.63 | 33.82 |
| AVG = | | | 1,997 | | 1,649 | | 1,609 | | 17.34 | 19.33 |

FIG. 11

CHICKEN FEED COMPOSITION AND METHOD OF FEEDING CHICKENS FOR PROMOTING HEALTH OR REJUVENATING EGG PRODUCTION

RELATED APPLICATION

This application claims the benefit of priority of U.S. provisional application Ser. No. 60/583,920, filed Jun. 29, 2004, which is relied on and incorporated herein by reference.

FIELD OF THE INVENTION

The present invention relates generally to a chicken feed composition and to a method for feeding chickens. More particularly, the present invention relates to a feed composition comprising pecan byproduct meal that provides certain advantages for promoting the health of laying hens or rejuvenating egg production in laying hens, and to a method of feeding laying hens using the feed composition.

BACKGROUND OF THE INVENTION

Modern breeds of laying hens initiate egg production just prior to twenty weeks of age, and maintain a high level of productivity for an extended period. However, after one year of continuous egg laying (i.e., by approximately seventy weeks of age), hens accumulate considerable body fat and produce eggs at a lower rate and with lower quality shells. For decades, it is known in the art that the rate and quality of eggs produced by laying hens may be rejuvenated by forcing the hens to cease egg production for a period of several weeks. This process, known as "forced molting," simulates natural molting events in which the hens substantially reduce their feed intake, thereby losing excess body weight, cease egg production, and replace their plumage. When egg production is reinitiated, a higher rate of lay is achieved with improved shell quality.

The most common method of forcing a cessation of egg production in hens is to remove feed for a period of ten to twelve days. Egg production quickly ceases, with body weight losses approximating 25%. While this technique has been highly successful, proponents of animal welfare object not only to the prolonged period of feed deprivation, but also to the 2% to 3% mortality frequently experienced by flocks during the forced molting period. Customer pressure on major egg purchasers has led to stipulations that eggs sold to certain firms not be from force molted flocks. Such pressure is expected to increase.

An alternative to accomplishing hen rejuvenation by complete feed withdrawal has been proposed, whereby flocks are given high fiber feeds with reduced levels of digestible carbohydrate. In such feeds, much of the corn component of the diet is replaced with fibrous feedstuffs such as wheat middlings, a by-product produced during the milling of wheat for flour, and soybean hulls, a by-product of soybean processing for oil and meal production. The objective of such low energy feeds is to reduce the calorie consumption of hens, leading to the desired body weight loss and reduction in egg production. Flock rejuvenation would thus be accomplished without the prolonged feed withdrawal that is of concern to animal welfare groups.

Several studies have been conducted and reported in the scientific literature describing attempts to achieve flock rejuvenation through the use of high fiber and low digestible carbohydrate diets. However, two problems have been observed that compromise the effectiveness of these conventional approaches.

First, hens are able to adjust the amount of feed consumed in accordance with the calorie content of the feed. Thus, when the energy of the feed is reduced, hens partially compensate by consuming greater amounts of feed. This compromises the effectiveness of programs designed to achieve molting without feed withdrawal. Second, very high fiber diets are of a bulky texture, and tend not to flow through modern feed manufacturing and delivery systems. Both problems have limited the success of non-feed withdrawal molting programs.

Therefore, a need exists for an improved reduced calorie feed composition for rejuvenating egg production in laying hens which does not lead to a compensatory increase in the amount of feed consumed, and which may be refined to a relatively small particle size.

In addition to rejuvenating egg production, high fiber feeds are also known to positively affect the health of hens through several potential mechanisms. For instance, dietary fiber affects the structure and function of the gut and may be used to correct intestinal problems, such as ulcers, in hens. Further, feeding hens dietary fiber reduces the potential for diarrhea. Moreover, high fiber feeds speed the elimination of excreta from the hen to assist in digestive cleaning. Accordingly, a need exists for an alternative high fiber feed that may be used to promote the health of laying hens.

SUMMARY OF THE INVENTION

The present invention answers this need by providing a chicken feed composition comprising pecan byproduct meal which causes a reduction in feed intake, and thereby provides the body weight loss and reduction in egg production desired for achieving flock rejuvenation. Further, the present invention provides a chicken feed composition comprising pecan byproduct meal that may be used as an alternative, high fiber feed for promoting the health of laying hens.

According to the present invention, a chicken feed composition comprises pecan byproduct meal. In one embodiment, the pecan byproduct meal constitutes at least about 3% by weight of the feed composition. In other embodiments, the pecan byproduct meal constitutes between about 3% by weight of the feed composition and about 15% by weight of the feed composition.

Pecan byproduct meal, described in greater detail below, is obtained during the commercial shelling of pecans. Although not a traditional ingredient for animal feeds, initial observations suggested that the material might have a beneficial role in achieving flock rejuvenation without feed withdrawal. This beneficial role may involve a synergistic effect of the pecan byproduct meal being used in combination with other fiber sources. Specifically, as shown in Study 1 described below, laying hens receiving feeds with only a small percentage of pecan byproduct meal (about 3% dry weight of the feed) were observed to significantly moderate feed consumption. This was particularly noted when pecan byproduct meal was incorporated into feeds together with wheat middlings and soybean hulls, the conventional components of high fiber and low digestible carbohydrate diets. Accordingly, in another embodiment, the chicken feed composition of the present invention further comprises a source of fiber. The source of fiber added to the feed composition of the present invention may comprise wheat middlings and soybean hulls, as well as additional or alternative sources of fiber as may be available. In one embodiment, the wheat middlings constitute about 30% by weight of the feed composition and the soybean hulls constitute about 30% by weight of the feed composition.

Furthermore, because the use of pecan byproduct meal reduces the amount of high fiber ingredients needed in the diet, physical characteristics of the feed are markedly improved.

Therefore, it is an object of the present invention to provide a reduced calorie chicken feed composition for rejuvenating egg production in laying hens that does not lead to a compensatory increase in the amount of feed consumed.

Another object of the present invention is to provide a reduced calorie chicken feed composition for rejuvenating egg production in laying hens which is not bulky in texture, and will flow through modern feed manufacturing and delivery systems.

A still other object of the present invention is to provide a high fiber chicken feed composition for promoting the health of laying hens.

Yet another object of the present invention is to provide a method of feeding laying hens using the feed composition for promoting the health of laying hens or for rejuvenating egg production in laying hens.

Further objects, features and advantages will become apparent upon consideration of the following detailed description of the invention when taken in conjunction with the drawings and the appended claims.

BRIEF DESCRIPTION OF THE DRAWINGS

FIG. 1 is a table showing the feed intake of hens taking part in a first study of the effects of the present invention during the week before commencement of the study.

FIG. 2 is a table showing the feed intake of hens taking part in a first study of the effects of the present invention during the fourteen-day period of the study.

FIG. 4 is a table showing the body weight of hens taking part in a first study of the effects of the present invention at certain points during the study.

FIG. 6 is a table showing the number of eggs produced by hens taking part in a first study of the effects of the present invention during the week before commencement of the study.

FIG. 7 is a table showing the number of eggs produced by hens taking part in a first study of the effects of the present invention during the fourteen-day period of the study.

FIG. 9 is a table showing the feed intake of hens taking part in a second study of the effects of the present invention during the seventeen-day period of the study.

FIG. 11 is a table showing the average body weight of hens taking part in a second study of the effects of the present invention at certain points during the study.

DETAILED DESCRIPTION OF THE INVENTION

Figure 3:
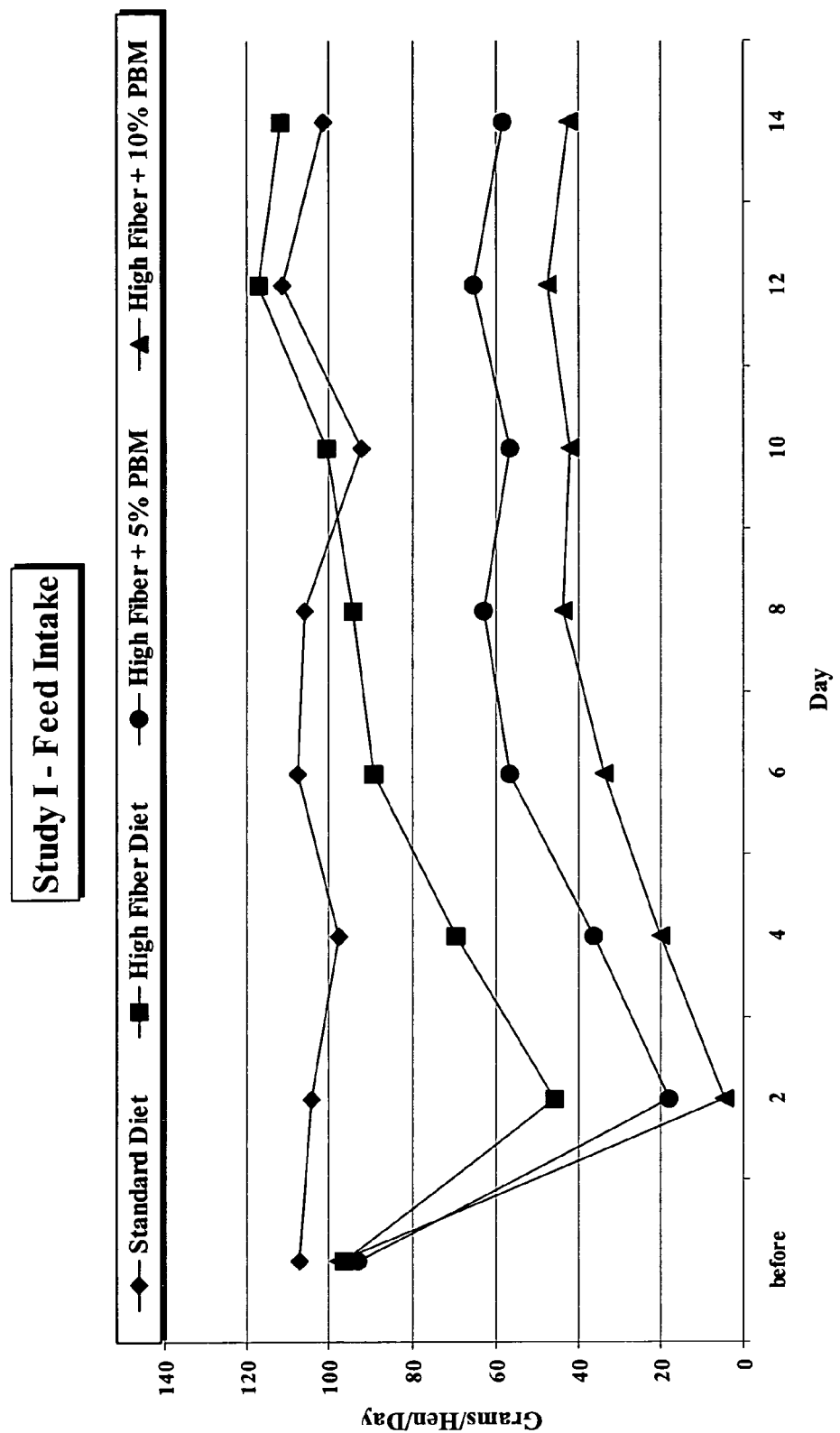
FIG. 3 is a graph illustrating the average daily feed intake for each diet for the hens taking part in a first study of the effects of the present invention.

The present invention provides a feed composition for promoting the health of laying hens or for rejuvenating egg production in laying hens comprising pecan byproduct meal. The present invention also provides a method for feeding laying hens that comprises feeding a laying hen a feed composition comprising pecan byproduct meal.

In accordance with the present invention, a feed composition for benefiting or rejuvenating chickens is provided comprising pecan byproduct meal. In one embodiment, the pecan byproduct meal constitutes at least about 3% by weight of the feed composition. In other embodiments, the pecan byproduct meal constitutes between about 3% by weight of the feed composition and about 15% by weight of the feed composition.

A pecan has three distinct parts: (1) a hard outer shell; (2) a meat portion; and (3) an inner liner portion, typically referred to as "packing tissue," located on the inside surface of the shell and between the shell and the meat portion. The packing tissue is generally soft in texture and reddish-brown in color.

The pecan byproduct meal used in accordance with one embodiment of the present invention consists primarily of the packing tissue and is derived from processing pecans. Particularly, in commercial pecan cracking operations the majority, but not all, of the meat is separated from the shell during a several step process. Typically, 1% to 3% of the meat (usually in small broken pieces) ends up in a pecan shell byproduct stream. The shell byproduct stream may then be processed to separate the hard shells from the packing tissue and from any residual meat. The packing tissue and residual meat separated from the shell byproduct stream, which may include small particles of shell, comprise the pecan byproduct meal that is used in the chicken feed composition of one embodiment of the present invention.

Therefore, in one embodiment, the pecan byproduct meal comprises about 100% pecan packing tissue. In another embodiment, the pecan byproduct meal comprises pecan packing tissue, a residual amount of pecan meat, and a residual amount of pecan shell.

In still other embodiments, the pecan byproduct meal may comprise pecan packing tissue and pecan shell with or without pecan meat.

In one embodiment, the feed analysis properties for the pecan byproduct meal of the present invention are as follows (dry basis):

TABLE 14

| | |
|---|---|
| Moisture | 18.49% |
| Crude Protein | 4.37% |
| Digestible Protein | 0.58% |
| Crude Fat | 7.97% |
| Crude Fiber | 16.06% |
| Nitrogen free extract | 69.79% |
| Total Digestible Nutrients | 81.65% |
| Ash | 1.81% |

In various other embodiments, the feed analysis properties for the pecan byproduct meal of the present invention are as follows (dry basis):

| | |
|---|---|
| Moisture | 4-20% |
| Crude Protein | 2-10% |
| Digestible Protein | 0-3% |
| Crude Fat | 4-12% |
| Crude Fiber | 10-30% |
| Nitrogen free extract | 50-80% |
| Total Digestible Nutrients | 65-90% |
| Ash | 1-5% |

Advantageously, the pecan byproduct meal of the present invention may be refined to a variety of particle sizes having a range of minus 8 U.S. Standard sieve mesh to a minus 325 U.S. Standard sieve mesh. Thus, the particle size of the present invention may be adapted to accommodate a variety of manufacturing and delivery systems.

EFFECT OF THE INVENTION

With reference to the following studies, the advantages of the present invention for the rejuvenation of laying hens will be described. It will be appreciated that while the following studies illustrate the present invention more specifically, the present invention is not restricted thereto. Hereinafter, "%" refers to % by weight, except when used in reference to "percent weight loss" and "percent of egg production," as described in greater detail below.

Study 1

A formal study was designed to test the hypothesis that pecan byproduct meal can enhance the beneficial effects of wheat middlings and soybean hulls in promoting the rejuvenation of laying hens without imposition of total feed withdrawal. In this study, sixty-three laying hens at sixty-eight weeks of age were presented with four dietary regimens (fifteen hens with regimen number 3 and sixteen hens each with regimen numbers 1, 2, and 4) for a period of fourteen days. During this time, feed intake, egg production, and changes in body weight were monitored. The dietary treatments used in this study were as follows:

1. A continuation of the normal laying hen feed (the "standard diet").
2. A high fiber diet with about 30% wheat middlings and about 30% soybean hulls (the "standard high fiber diet").
3. The standard high fiber diet with about 5% pecan byproduct meal added thereto.
4. The standard high fiber diet with about 10% pecan byproduct meal added thereto.

The specific composition of Diet Nos. 1-4 is listed in Table 1, below.

TABLE 1

Composition of Diet Nos. 1-4.

| Composition | Diet No. 1 | Diet No. 2 | Diet No. 3 | Diet No. 4 |
|---|---|---|---|---|
| Wheat Middlings (%) | — | 31.4 | 29.8 | 28.3 |
| Soybean Hulls (%) | — | 30.0 | 28.5 | 27.0 |
| Corn, Yellow (%) | 62.8 | 29.8 | 28.3 | 26.9 |
| Soy Meal 47.5% (%) | 24.6 | — | — | — |
| Limestone (%) | 9.1 | 7.6 | 7.2 | 6.8 |
| Dicalcium (22/18.5) (%) | 1.4 | 0.65 | 0.62 | 0.59 |
| Fat Animal & Vegetable (%) | 1.3 | — | — | — |
| Salt (%) | 0.43 | 0.41 | 0.39 | 0.37 |
| Tr min/BR. (Mineral) (%) | 0.50 | 0.07 | 0.07 | 0.06 |
| Vit PMX-Broil (Vitamins) (%) | 0.10 | 0.05 | 0.05 | 0.05 |
| Meth DL-98 | 0.09 | — | — | — |
| Pecan Byproduct Meal (%) | — | — | 5.0 | 10.0 |
| TOTAL: | 100.0 | 100.0 | 100.0 | 100.0 |
| Bushel Weight (lbs/Bu) | | 34.75 | 34.45 | 34.20 |

The nutrient contents of Diet No. 1, the standard diet, per pound (lbs) are listed in Table 2, below.

TABLE 2

Nutrient Contents of Diet No. 1.

| | |
|---|---|
| Metabolizable Energy (kcal/kg) | 2,839.2 |
| Metabolizable Energy (cal/lb) | 1,290.0 |
| Crude Protein (%) | 17.0 |
| Arginine (%) | 1.1 |
| Lysine (%) | 0.9 |
| Methionine (%) | 0.4 |
| Meth & Cystin (%) | 0.7 |
| Tryptophane (%) | 0.2 |
| Crude Fat (%) | 3.9 |
| Crude Fiber (%) | 2.31 |
| Calcium (%) | 3.9 |
| Phosphorus-Av (%) | 0.4 |
| Phosphorus-To (%) | 0.6 |
| Sodium (%) | 0.2 |
| Xanthodphyll (mg/lb) | 6.3 |
| Choline (mg/lb) | 283.0 |

The nutrient contents of Diet No. 2, the standard high fiber diet, per pound (lbs) are listed in Table 3, below.

TABLE 3

Nutrient Contents of Diet No. 2.

| | |
|---|---|
| Metabolizable Energy (kcal/kg) | 1870.0 |
| Metabolizable Energy (cal/lb) | 850.0 |
| Crude Protein (%) | 10.2 |
| Arginine (%) | 0.5 |
| Lysine (%) | 0.4 |
| Methionine (%) | 0.1 |
| Meth+Cystin (%) | 0.3 |
| Tryptophane (%) | 0.1 |
| Crude Fat (%) | 2.6 |
| Crude Fiber (%) | 14.9 |
| Calcium (%) | 3.3 |
| Phosphorus-Av (%) | 0.3 |
| Phosphorus-To (%) | 0.5 |
| Sodium (%) | 0.2 |
| Xanthodphyll (mg/lb) | 3.0 |
| Choline (mg/lb) | 400.7 |

In other embodiments, the composition of a high fiber diet to which pecan byproduct meal may be added in accordance with the present invention may comprise about 50% wheat middlings and about 30% soybean hulls, or about 40% wheat middlings and about 30% soybean hulls. Table 4, below, shows the specific composition of such other embodiments.

TABLE 4

Possible Composition of Other High Fiber Diets.

|  | High Fiber Diet X | High Fiber Diet Y |
|---|---|---|
| Wheat Middlings (%) | 50.1 | 40.8 |
| Soybean Hulls (%) | 30.0 | 30.0 |
| Corn, Yellow (%) | 11.3 | 20.5 |
| Limestone (%) | 7.7 | 7.6 |
| Dicalcium (22/18.5) (%) | 0.46 | 0.56 |
| Salt (%) | 0.4 | 0.4 |
| Tr min/BR. (Mineral) (%) | 0.07 | 0.07 |
| Vit PMX-Broil (Vitamins) (%) | 0.05 | 0.05 |
| TOTAL: | 100.0 | 100.0 |

It will be appreciated that other suitable diet compositions may be used in connection with the present invention to effectively promote hen health or egg production rejuvenation in laying hens. Such other suitable diets may include, without limitation, the following: rice meal, rice hulls, beet pulp, and/or any other agricultural residue, food grade, or pet food grade ingredient (e.g., off spec material or out of date material).

Feed Intake.

With reference to FIG. 1, a Feed Intake (Before) Table shows the average amount of feed consumed (in grams) for each diet per hen per day during the week before the study. Particularly, sixty-three hens were housed two per cage (resulting in thirty-two rows, with Row 15 representing a single hen in a cage) and each dietary regimen (identified in column "Tt") was fed to eight cages every other day. For each cage, the amount of feed provided ("IN") and the remaining amount of feed removed before the next feeding ("OUT") was measured, and the average amount of feed consumed per hen per day ("INTAKE") was calculated. In addition, the INTAKE values were used to calculate the average daily feed intake ("AVG") for the five-day period. For example, Row 1 shows that 600.0 grams ("IN") of Diet No. 1 ("Tt") was fed to Cage 1 (containing 2 hens) on April 26 and that 108.8 grams ("OUT") of Diet No. 1 remained unconsumed on Day 2. Accordingly, the average feed intake of each hen in Cage 1 per day over the two-day period was calculated to be 122.8 grams/hen/day as ((600.0 minus 108.8) divided by 2) divided by 2.

Table 5, below, shows the average of the feed intake calculations ("INTAKE") from FIG. 1 for each diet.

TABLE 5

Average Daily Feed Intake Per Diet (Before)

| Tt | Average |
|---|---|
| 1 | 107.0 |
| 2 | 96.4 |
| 3 | 92.9 |
| 4 | 97.5 |

With reference to FIG. 2, a Feed Intake Table shows the average amount of feed consumed (in grams) for each diet per hen per day during the fourteen-day period of the study. Particularly, sixty-three hens were housed two per cage (resulting in thirty-two rows, with Row 15 representing a single hen in a cage) and each dietary regimen (identified in column "Tt") was fed to eight cages every other day. For each cage, the amount of feed provided ("IN") and the remaining amount of feed removed before the next feeding ("OUT") was measured, and the average amount of feed consumed per hen per day ("INTAKE") was calculated. For example, Row 1 shows that 500.0 grams ("IN") of Diet No. 1 ("Tt") was fed to Cage 1 (containing 2 hens) at the start of the study and that 56.5 grams ("OUT") of Diet No. 1 remained unconsumed on Day 2. Accordingly, the average feed intake of each hen in Cage 1 per day over the two-day period was calculated to be 110.9 grams/hen/day as ((500.0 minus 56.5) divided by 2) divided by 2.

Table 6, below, shows the average of the feed intake calculations ("INTAKE") from FIG. 2 for each diet. Particularly, each row of Table 6 shows the average feed intake (in grams) per hen per day for all hens on each diet ("Tt") as measured every other day of the study. For example, Row 1 of Table 6 shows that the hens receiving Diet No. 1 ("Tt") consumed an average of 104.25 grams of feed per day during Days 1 and 2, an average of 97.49 grams of feed per day during Days 3 and 4, and an average of 107.38 grams of feed per day during days 5 and 6.

TABLE 6

Average Daily Feed Intake Per Diet.

Average Feed Intake (in grams) Per Hen Per Day

| Tt | Day 2 | Day 4 | Day 6 | Day 8 | Day 10 | Day 12 | Day 14 |
|---|---|---|---|---|---|---|---|
| 1 | 104.25 | 97.49 | 107.38 | 105.75 | 91.98 | 111.45 | 101.35 |
| 2 | 45.89 | 69.76 | 89.19 | 94.25 | 100.28 | 116.95 | 111.79 |
| 3 | 17.82 | 36.19 | 56.50 | 62.72 | 55.78 | 65.52 | 58.50 |
| 4 | 4.47 | 19.85 | 33.66 | 43.72 | 42.22 | 47.44 | 42.68 |

With reference to FIG. 3, the average daily feed intake for each diet is illustrated graphically.

Table 7, below, shows the average daily energy intake (in kilocalories) per day for Day 3 through Day 14 for each diet. (Days 1 and 2, during which the chickens were experiencing a transitional state due to receipt of a new feed, have been omitted). For example, Row 1 shows that the average daily energy intake (in kilocalories) per bird per day for Diet No. 1, the standard diet, was calculated to be 291 kilocalories as 102.57 (the average feed intake (in grams) per hen per day for Days 4 through 14 for Diet No. 1, using data from Table 6, above) multiplied by 2.839 kilocalories per gram (using metabolizable energy data from Table 2, above). In addition, the average daily energy intake (in kilocalories) per kilogram of body weight per day for Diet 1 was calculated to be 156 kilocalories as 291 kilocalories per bird divided by 1.87 kilograms per bird (the average weight of all birds receiving Diet No. 1 before and after the study, calculated using data from FIG. 4, described below). Similar calculations were performed for Diets 2 through 4 using 1.870 kilocalories per gram as the metabolizable energy of each diet (Table 3). (It was presumed that Diet No. 3 and Diet No. 4 consisted of relatively the same amount of metabolizable energy as Diet No. 2, the standard high fiber diet.)

TABLE 7

Kilocalorie Intake Per Diet.

| Tt | Per Bird Per Day | Per Kg Body Wt. Per Day | Per Lb Body Wt. Per Day |
|---|---|---|---|
| 1 | 291 | 156 | 71 |
| 2 | 181 | 103 | 47 |
| 3 | 105 | 62 | 28 |
| 4 | 72 | 44 | 20 |

Body Weight.

With reference to FIG. 4, a Body Weight Table shows the body weight (in grams) for each hen at the start of the study and at the end of each week of the study. Particularly, the weight of each hen of each cage ("Bird 1" and "Bird 2," respectively) was measured at the start of the study, on Day 7, and on Day 14. In addition, the average weight of the hens in each cage was calculated for each of the aforementioned instances ("Avg."). For example, Row 1 shows that the first bird in the first cage ("Bird 1"), which received Diet No. 1 ("Tt"), weighed 1980 grams at the start of the study and that the second bird in the first cage ("Bird 2"), which also received Diet No. 1 ("Tt"), weighed 1855 grams at the start of the study. Accordingly, the average weight of each hen in Cage 1 was calculated to be 1917.5 grams as (1980 plus 1855) divided by 2.

Table 8, below, shows the average body weight of all hens on each diet at the start of the study and at the end of each week of the study. Particularly, each row of Table 8 shows the average body weight (in grams) of all hens on each diet ("Tt") as measured at the start of the study, on Day 7, and on Day 14. In addition, the average percent weight loss ("% Loss") was calculated for all hens on each diet over the course of the study. For example, Row 1 shows that the hens that received Diet No. 1 ("Tt") weighed an average of 1912.6 grams at the start of the study, an average of 1854.6 grams on Day 7, and an average of 1835.3 grams on Day 14. Accordingly, the average weight loss as a percent of body weight was calculated to be 4.0% as (1912.6 minus 1835.3) divided by 1912.6.

TABLE 8

Average Body Weight and Percent Weight Loss Per Diet.

| Tt | Body Weight (g) | | | % Loss |
|---|---|---|---|---|
| | Start | Day 7 | Day 14 | |
| 1 | 1912.6 | 1854.6 | 1835.3 | 4.0 |
| 2 | 1907.6 | 1682.3 | 1667.8 | 12.6 |
| 3 | 1906.5 | 1611.0 | 1560.8 | 18.1 |
| 4 | 1907.6 | 1529.6 | 1464.2 | 23.2 |

Figure 5:
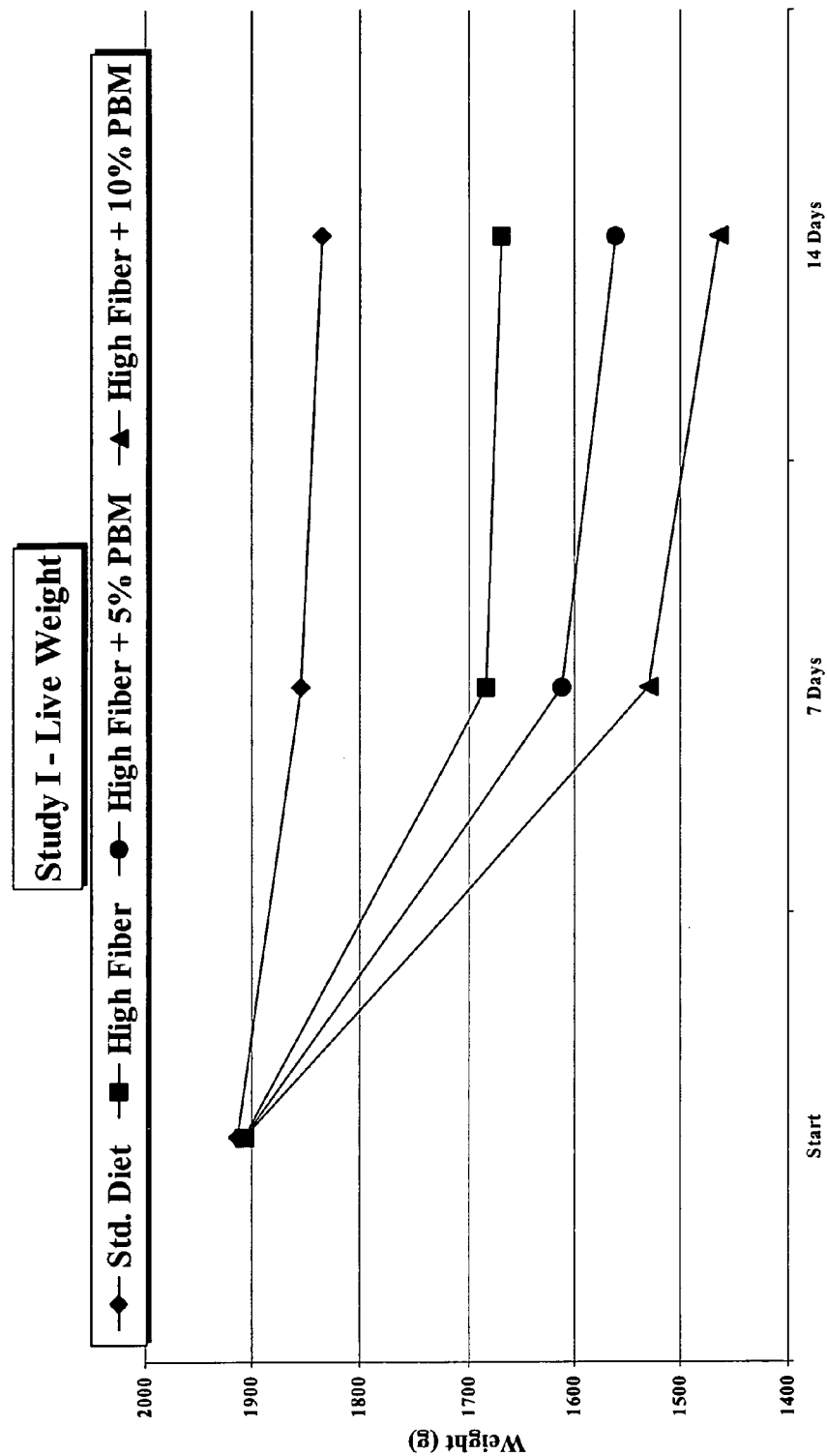
FIG. 5 is a graph illustrating the average body weight for each diet for the hens taking part in a first study of the effects of the present invention at certain points during the study.

With reference to FIG. 5, the average body weight of all hens on each diet at the start of the study and at the end of each week of the study is illustrated graphically.

Egg Production.

In this section, as known in the art, "%" when used to refer to percent of egg production represents the number of eggs produced per hen per day, expressed as a percent, e.g., ten eggs by ten hens in a single day equals 100%.

With reference to FIG. 6, an Egg Production (Before) Table shows the number of eggs produced by all hens during the week before the study.

Table 9, below, shows the total number of eggs produced by all hens per diet during the week before the study. In addition, the percent of egg production was calculated and is included in Table 9. For example, Row 1 shows that the total number of eggs produced by hens receiving Diet No. 1 was calculated to be 83 eggs using the data from FIG. 6. In addition, the percent of egg production for hens receiving Diet No. 1 was calculated to be 74.1% as 83 eggs divided by 16 hens divided by 7 days, expressed as a percent.

TABLE 9

Egg Production Total Per Diet (Before).

| Tt | Eggs | % |
|---|---|---|
| 1 | 83 | 74.1 |
| 2 | 85 | 75.9 |
| 3 | 87 | 77.7 |
| 4 | 80 | 71.4 |

With reference to FIG. 7, an Egg Production Table shows the number of eggs produced by all hens throughout the study.

Table 10, below, shows the number of eggs produced by all hens on each diet throughout the study. Particularly, the number of eggs produced by all hens on each diet was counted each day and the percent of egg production was calculated. For example, Row 1 of Table 10 shows that before the study, the hens receiving Diet No. 1 were laying eggs at 74% of egg production (as calculated above) and that on Day 1, such hens laid a total of 6 eggs which was calculated to be 38% of egg production as 6 eggs divided by 16 hens divided by 1 day, expressed as a percent.

TABLE 10

Egg Production Per Diet.

| Tt | Before | | Day 1 | | Day 2 | | Day 3 & 4 | | Day 5 & 6 | | Day 7 & 8 | | Day 9 & 10 | | Day 11 & 12 | | Day 13 & 14 | |
|---|---|---|---|---|---|---|---|---|---|---|---|---|---|---|---|---|---|---|
| | Num | % | Num | % | Num | % | Num | % | Num | % | Num | % | Num | % | Num | % | Num | % |
| 1 | — | 74 | 6 | 38 | 17 | 106 | 25 | 78 | 26 | 81 | 30 | 94 | 22 | 69 | 28 | 88 | 24 | 78 |
| 2 | — | 76 | 5 | 31 | 13 | 81 | 15 | 47 | 11 | 34 | 14 | 44 | 12 | 38 | 11 | 34 | 14 | 44 |
| 3 | — | 78 | 7 | 44 | 13 | 81 | 7 | 22 | 8 | 25 | 3 | 9 | 2 | 6 | 3 | 9 | 5 | 16 |
| 4 | — | 71 | 4 | 25 | 8 | 50 | 4 | 13 | 2 | 6 | 0 | 0 | 1 | 3 | 0 | 0 | 0 | 0 |
| Tot. | — | | 22 | | 51 | | 51 | | 47 | | 47 | | 37 | | 42 | | 44 | |

Figure 8:
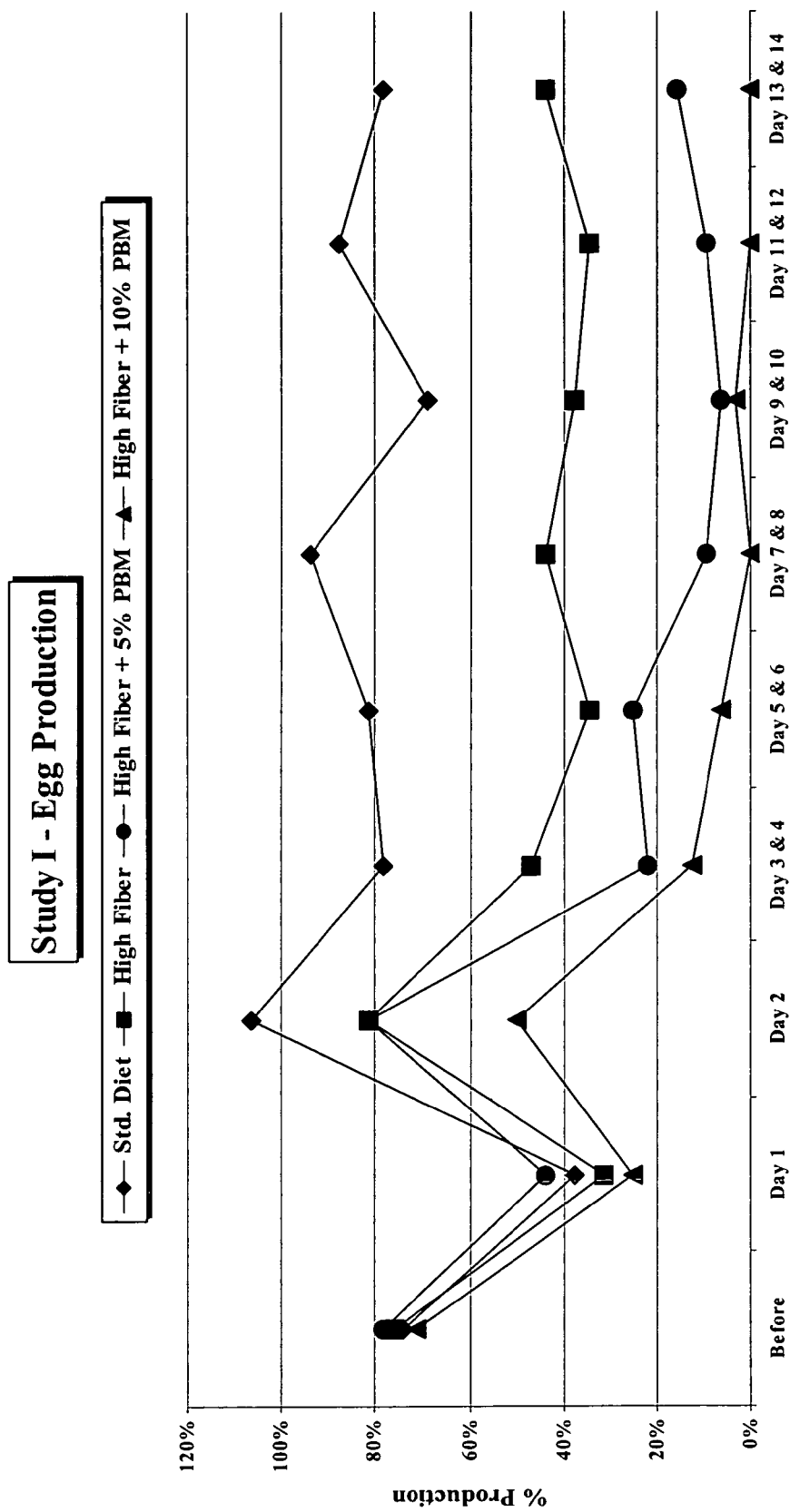
FIG. 8 is a graph illustrating the egg production for each diet for the hens taking part in a first study of the effects of the present invention.

With reference to FIG. 8, the egg production of all hens on each diet as a percent of egg production is illustrated graphically.

Observations.

With reference to FIG. 3, consumption of Diet No. 2, the standard high fiber diet, was initially reduced, but after 10 days consumption reached the level of intake of hens continuing to receive Diet No. 1, the standard diet. However, with reference to the intake per bird per day data of Table 7, because Diet No. 2 was lower in energy than Diet No. 1, kilocalorie consumption of hens in this regimen was reduced by approximately 38%. Notably, Diet No. 3, with about 5% pecan byproduct meal, was almost twice as effective as Diet No. 2 in reducing kilocalorie consumption. In addition, Diet No. 3 reduced kilocalorie consumption by about 64% when compared to Diet No. 1, the standard diet. Moreover, hens receiving Diet No. 4, with about 10% pecan byproduct meal, consumed only 25% of the kilocalories of hens receiving the standard diet (a 75% reduction).

With reference to Table 8, above, body weight losses averaged 12.6% for hens receiving Diet No. 2, 18.1% for hens receiving Diet No. 3, and 23.2% for hens receiving Diet No. 4.

With reference to FIG. 8, hens receiving Diet No. 1, the standard diet, continued egg production in a normal manner after transitioning to the new diet, indicating satisfactory experimental conditions. Egg production never ceased in hens receiving Diet No. 2, and was only reduced to about 50% of that of Diet No. 1, the standard diet. By contrast, egg production of hens receiving Diet No. 3 dropped to about 12% that of hens receiving the standard diet. Further, hens receiving Diet No. 4 experienced a virtual cessation of egg production after 7 days.

The results of Study 1 demonstrate that the amount of pecan byproduct meal in a feed composition is inversely related to feed consumption and egg production, and directly related to weight loss in hens.

Study 2.

A second formal study was designed to test the range of application of the pecan byproduct meal in enhancing the effects of diets in promoting the rejuvenation of laying hens without imposition of total feed withdrawal. In this study, ninety-six laying hens aged sixty-eight weeks of age were presented with six dietary regimens (sixteen hens per regimen) for a period of seventeen days. During this time, feed intake, egg production, and changes in body weight were monitored. The dietary regimens used in this study were as follows:

A. A standard high fiber diet with about 30% wheat middlings and about 30% soybean hulls (the "standard high fiber diet").
B. The standard high fiber diet with about 3% pecan byproduct meal added thereto.
C. The standard high fiber diet with about 6% by weight of pecan byproduct meal added thereto.
D. The standard high fiber diet with about 9% pecan byproduct meal added thereto.
E. The standard high fiber diet with about 12% pecan byproduct meal added thereto.
F. The standard high fiber diet with about 15% pecan byproduct meal added thereto.

The specific composition of Diet A, the standard diet, is listed in Table 11, below.

TABLE 11

Composition of Diet A.

| Composition | Diet No. 1 (%) |
| --- | --- |
| Wheat Middlings | 32.2 |
| Soybean Hulls | 32.2 |
| Corn, Yellow | 26.6 |
| Limestone | 7.4 |
| Dicalcium (22/18.5) | 0.9 |
| Salt | 0.4 |
| Tr min/BR. (Mineral) | 0.07 |
| Vit PMX-Broil (Vitamins) | 0.05 |
| Pecan Byproduct Meal | — |
| TOTAL: | 100.0 |

As previously stated, it will be appreciated that other suitable diet compositions, including, without limitation, the above-identified diet compositions of Study 1, may be used in connection with the present invention to effectively promote egg production rejuvenation in laying hens.

Feed Intake.

Figure 9:
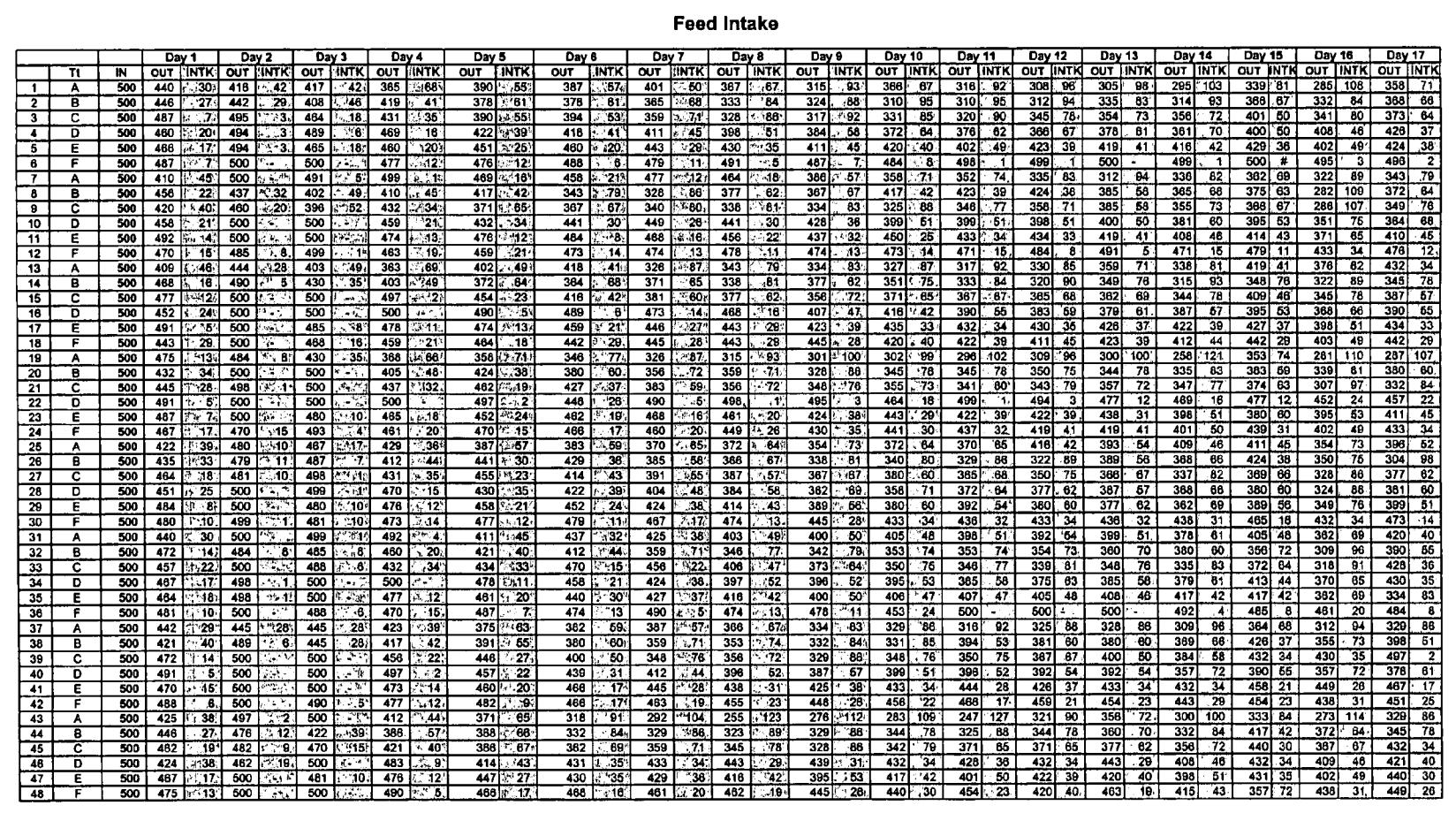

With reference to FIG. 9, a Feed Intake Table shows the average amount of feed consumed (in grams) for each diet per day per hen during the seventeen day period of the study. Particularly, ninety-six hens were housed two per cage (resulting in forty-eight rows) and 500 grams ("Feed In") of each dietary regimen (identified in column "Tt") was fed to eight cages each day. For each cage, the remaining amount of feed removed before the next feeding ("OUT") was measured, and the average amount of feed consumed per hen per day ("INTK") was calculated. For example, Row 1 shows that 500.0 grams ("Feed In") of Diet A ("Tt") was fed to Cage 1 (containing 2 hens) at the start of the study and that 440 grams ("OUT") of Diet A remained unconsumed at the end of Day 1. Accordingly, the average feed intake of each hen in Cage 1 per day was calculated to be 30 grams/hen/day as (500.0 minus 440) divided by 2.

Table 12, below, shows the average of the daily feed intake calculations from FIG. 9 for each diet. Particularly, each row of Table 12 shows the average feed intake (in grams) per hen per day for all hens on each diet ("Tt") as measured each day of the study. For example, Row 1 of Table 12 shows that the hens receiving Diet A ("Tt") were consuming an average of 92 grams of feed before the study commenced ("B"), consumed an average of 34 grams of feed on Day 1, and consumed an average of 15 grams of feed on Day 2.

TABLE 12

Average Daily Feed Intake Per Diet.

Average Feed Intake (in grams) Per Hen Per Day

| Tt | B | 1 | 2 | 3 | 4 | 5 | 6 | 7 | 8 | 9 | 10 | 11 | 12 | 13 | 14 | 15 | 16 | 17 |
| --- | --- | --- | --- | --- | --- | --- | --- | --- | --- | --- | --- | --- | --- | --- | --- | --- | --- | --- |
| A | 92 | 34 | 15 | 22 | 41 | 52 | 54 | 62 | 70 | 81 | 79 | 87 | 79 | 78 | 86 | 63 | 90 | 69 |
| B | 93 | 27 | 13 | 26 | 43 | 49 | 61 | 72 | 75 | 79 | 76 | 74 | 75 | 69 | 76 | 57 | 84 | 69 |
| C | 94 | 20 | 5 | 12 | 29 | 39 | 47 | 61 | 69 | 78 | 75 | 75 | 73 | 66 | 74 | 52 | 80 | 52 |
| D | 95 | 19 | 3 | 1 | 8 | 24 | 28 | 32 | 36 | 44 | 48 | 47 | 49 | 47 | 56 | 45 | 60 | 47 |
| E | 96 | 11 | 1 | 7 | 14 | 20 | 22 | 28 | 33 | 44 | 39 | 42 | 41 | 41 | 47 | 41 | 55 | 43 |

TABLE 12-continued

Average Daily Feed Intake Per Diet.

Average Feed Intake (in grams) Per Hen Per Day

| Tt | B | 1 | 2 | 3 | 4 | 5 | 6 | 7 | 8 | 9 | 10 | 11 | 12 | 13 | 14 | 15 | 16 | 17 |
|---|---|---|---|---|---|---|---|---|---|---|---|---|---|---|---|---|---|---|
| F | 97 | 13 | 3 | 5 | 14 | 14 | 15 | 16 | 17 | 22 | 25 | 20 | 23 | 20 | 27 | 24 | 31 | 19 |
| AVG | 94.5 | 20.5 | 6.5 | 12.0 | 24.7 | 33.0 | 38.0 | 45.2 | 50.0 | 57.9 | 56.7 | 57.4 | 56.6 | 53.4 | 60.9 | 47.0 | 66.5 | 49.6 |

Figure 10:
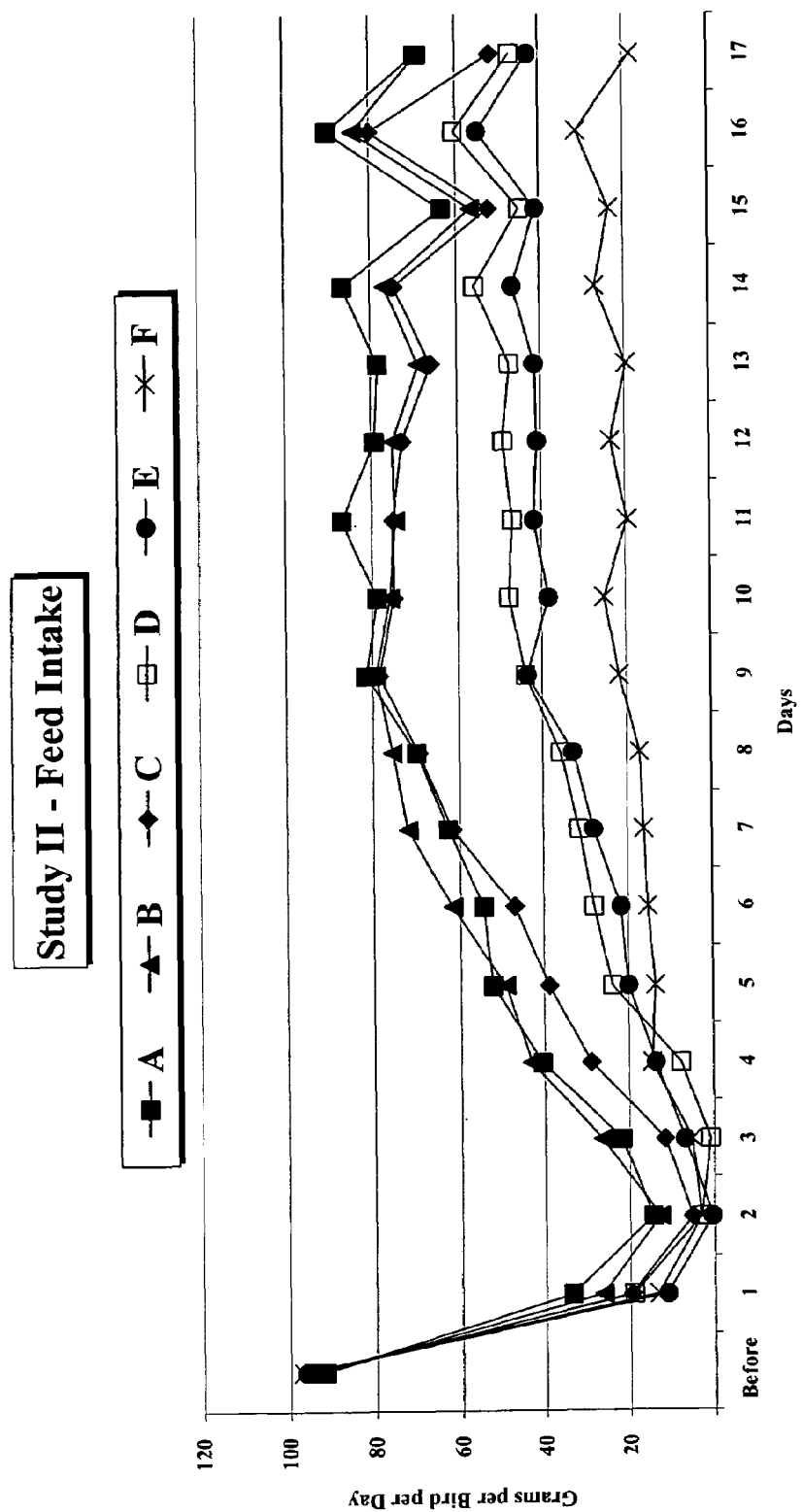
FIG. 10 is a graph illustrating the average daily feed intake for each diet for the hens taking part in a second study of the effects of the present invention.

With reference to FIG. 10, the average daily feed intake for each diet is illustrated graphically.

Body Weight.

With reference to FIG. 11, a Body Weight Table shows the body weight (in grams) for each hen (averaged by cage) at the start of the study and at the end of each week of the study. Particularly, the weight of the hens in each cage ("CAGE") was measured and the average weight of each bird in each cage ("BIRD") was calculated at the start of the study, on Day 7, and on Day 14. In addition, the average percent weight loss was calculated for each hen at Day 7 and Day 14. For example, Row 1 shows that the hens in Cage 1 ("CAGE"), which received Diet A ("Tt"), weighed a total of 3920 grams at the start of the study. Accordingly, the average weight of each hen in Cage 1 was calculated to be 1960 grams as 3920 divided by 2.

Table 13, below, shows the average body weight of all hens on each diet at the start of the study and at the end of each week of the study. Particularly, each row of Table 13 shows the average body weight (in grams) of all hens on each diet ("Tt") as measured at the start of the study, on Day 7, and on Day 14. In addition, the average percent weight loss ("% Loss") was calculated for all hens on each diet over the entire study. For example, Row 1 shows that the hens which received Diet A ("Tt") weighed an average of 1,937 grams at the start of the study, an average of 1,660 grams on Day 7, and an average of 1,651 grams on Day 14. Accordingly, the average weight loss as a percent of body weight between Day 7 and Day 14 was calculated to be 14.8% as (1,937 minus 1,651) divided by 1,937.

TABLE 13

Average Body Weight and Percent Weight Loss Per Diet.

| | Body Weight (g) | | | |
|---|---|---|---|---|
| Tt | Start | Day 7 | Day 14 | % Loss |
| A | 1,937 | 1,660 | 1,651 | 14.8 |
| B | 2,006 | 1,713 | 1,698 | 15.4 |
| C | 2,011 | 1,707 | 1,690 | 16.0 |
| D | 2,061 | 1,693 | 1,661 | 19.4 |
| E | 1,967 | 1,551 | 1,493 | 24.1 |
| F | 2,001 | 1,573 | 1,459 | 27.1 |
| AVG. | 1,997 | 1,649 | 1,609 | 19.5 |

Figure 12:
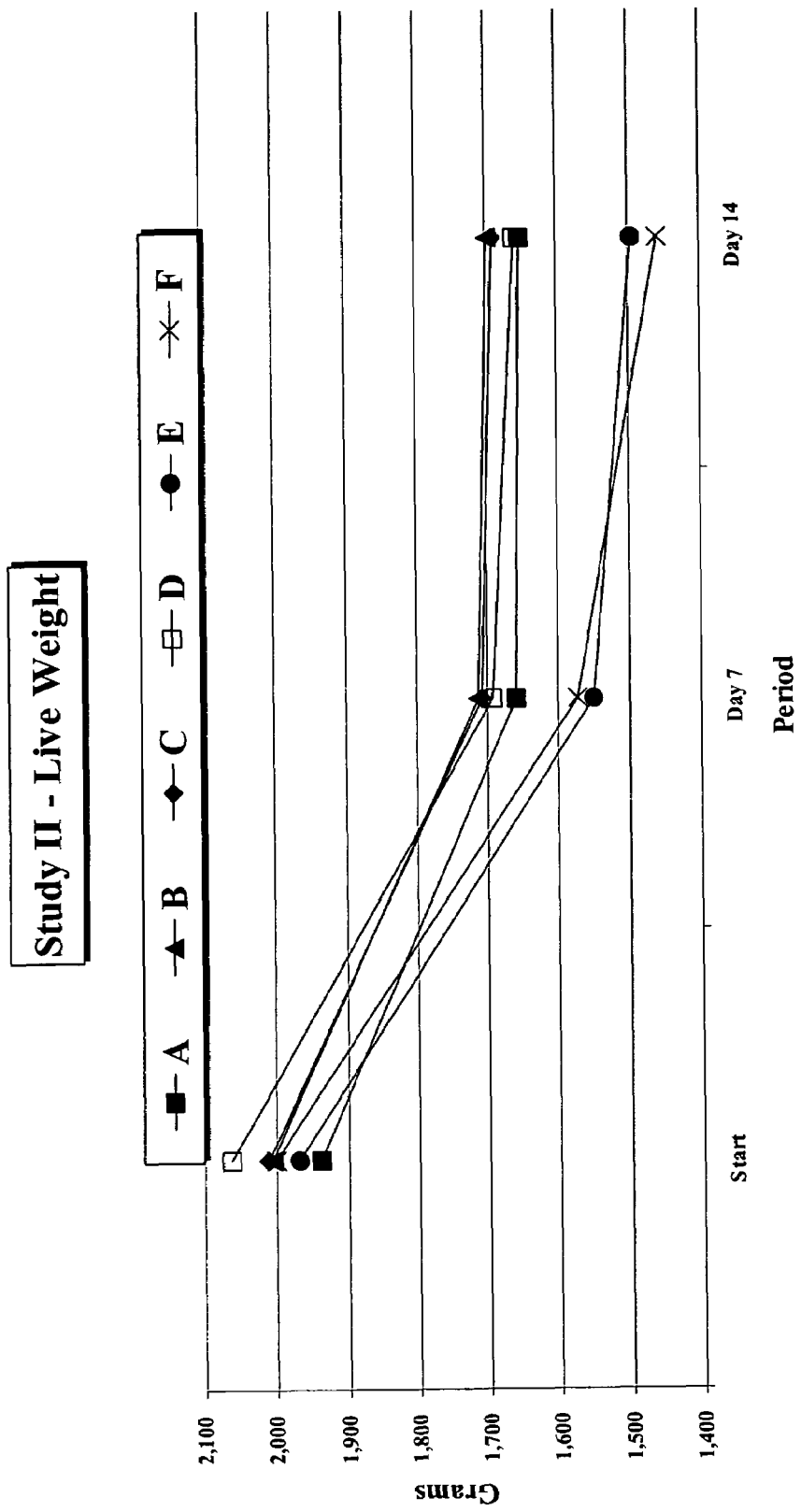
FIG. 12 is a graph illustrating the average body weight for each diet for the hens taking part in a second study of the effects of the present invention at certain points during the study.

With reference to FIG. 12, the average body weight of all hens on each diet at the start of the study and at the end of each week of the study is illustrated graphically.

Egg Production.

In this section, as known in the art, "%" when used to refer to percent of egg production represents the number of eggs produced per hen per day, expressed as a percent, e.g., ten eggs in ten days for a single hen equals 100%.

Table 14, below, shows the number of eggs produced by all hens on each diet for each day throughout the study.

TABLE 14

Egg Production Per Diet Per Day.

Eggs Produced Per Day

| Tt | B | 1 | 2 | 3 | 4 | 5 | 6 | 7 | 8 | 9 | 10 | 11 | 12 | 13 | 14 | 15 | 16 | 17 |
|---|---|---|---|---|---|---|---|---|---|---|---|---|---|---|---|---|---|---|
| A | 64 | 14 | 8 | 6 | 7 | 5 | 2 | 1 | 2 | 2 | 1 | 0 | 3 | 2 | 3 | 3 | 5 | 8 |
| B | 62 | 14 | 7 | 9 | 5 | 4 | 2 | 1 | 0 | 0 | 0 | 0 | 1 | 0 | 3 | 4 | 5 | 2 |
| C | 68 | 13 | 7 | 6 | 6 | 1 | 1 | 0 | 0 | 0 | 0 | 1 | 0 | 0 | 1 | 2 | 2 | 1 |
| D | 64 | 12 | 6 | 4 | 1 | 1 | 0 | 0 | 0 | 0 | 0 | 0 | 0 | 1 | 0 | 0 | 1 | 0 |
| E | 65 | 13 | 6 | 6 | 5 | 1 | 1 | 0 | 1 | 0 | 0 | 0 | 0 | 0 | 0 | 0 | 1 | 0 |
| F | 61 | 14 | 10 | 3 | 4 | 0 | 0 | 0 | 0 | 0 | 0 | 0 | 0 | 0 | 0 | 0 | 0 | 0 |
| TOT | 384 | 80 | 44 | 34 | 28 | 12 | 6 | 2 | 3 | 2 | 1 | 1 | 4 | 3 | 7 | 9 | 14 | 11 |

Table 15, below, shows the percent of egg production of all hens on each diet for each day throughout the study. Particularly, the number of eggs produced by all hens on each diet each day, as shown in Table 14, was used to calculate the percent of egg production. For example, Row 1 of Table 15 shows that on Day 1, the percent of egg production of hens receiving Diet A was calculated to be 88% as 14 eggs divided by 16 hens divided by 1 day, expressed as a percent.

TABLE 15

Egg Production % Per Day

| Tt | 1 | 2 | 3 | 4 | 5 | 6 | 7 | 8 | 9 | 10 | 11 | 12 | 13 | 14 | 15 | 16 | 17 |
|---|---|---|---|---|---|---|---|---|---|---|---|---|---|---|---|---|---|
| A | 88 | 50 | 38 | 44 | 31 | 13 | 6 | 13 | 13 | 6 | 0 | 19 | 13 | 19 | 19 | 31 | 50 |
| B | 88 | 44 | 56 | 31 | 25 | 13 | 6 | 0 | 0 | 0 | 0 | 6 | 0 | 19 | 25 | 31 | 13 |
| C | 81 | 44 | 38 | 38 | 6 | 6 | 0 | 0 | 0 | 0 | 6 | 0 | 0 | 6 | 13 | 13 | 6 |
| D | 75 | 38 | 25 | 6 | 6 | 0 | 0 | 0 | 0 | 0 | 0 | 0 | 6 | 0 | 0 | 6 | 0 |
| E | 81 | 38 | 38 | 31 | 6 | 6 | 0 | 6 | 0 | 0 | 0 | 0 | 0 | 0 | 0 | 6 | 0 |
| F | 88 | 63 | 19 | 25 | 0 | 0 | 0 | 0 | 0 | 0 | 0 | 0 | 0 | 0 | 0 | 0 | 0 |
| AVG | 83 | 46 | 35 | 29 | 13 | 6 | 2 | 3 | 2 | 1 | 1 | 4 | 3 | 7 | 9 | 15 | 11 |

Figure 13:
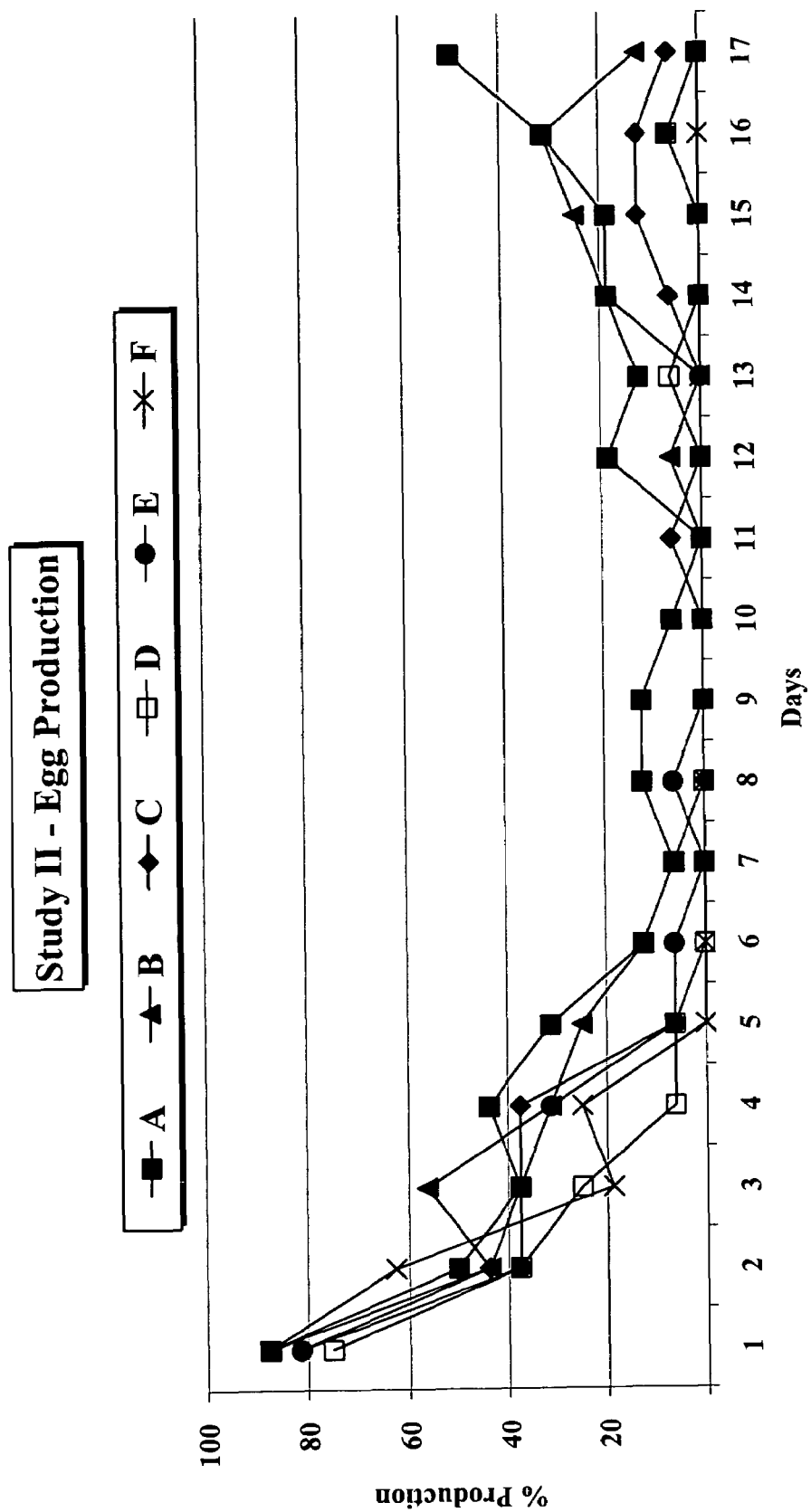
FIG. 13 is a graph illustrating the egg production for each diet for the hens taking part in a second study of the effects of the present invention.

With reference to FIG. 13, the egg production of all hens on each diet for each day is illustrated graphically.

Observations.

With reference to FIG. 10, feed intake declined rapidly for the first two days in hens receiving all diets, to less than 20 grams/day. The feed intake of hens receiving diets having 0% to about 6% pecan byproduct meal (Diets A, B, and C) increased to approximately 80 grams/day by Day 9 and then remained generally constant thereafter. The feed intake of hens receiving diets having about 9% and about 12% pecan byproduct meal (Diets D and E) increased to, and leveled off at, approximately 40-50 grams/day. The feed intake of hens receiving diets having about 15% pecan byproduct meal (Diet F) gradually increased and leveled off at approximately 20 grams/day by Day 9.

With reference to FIG. 12, weight loss was most pronounced (over 25%) for hens receiving diets having about 12% and about 15% pecan byproduct meal (Diets E and F). Hens receiving all other diets, by comparison, averaged approximately 15% weight loss.

With reference to FIG. 13, egg production sharply declined in hens receiving all diets for the first two days. A sharp decline in production continued after Day 2 in hens receiving diets having at least about 9% pecan byproduct meal (Diets D, E, and F). Hens receiving Diets A, B, and C, however, experienced a staggered decline in production from Day 2 to Day 8. Hens receiving diets comprising pecan byproduct meal (Diets B-F) began ceasing production starting on Day 5 and had virtually stopped production by Day 8. In contrast, hens receiving the standard high fiber diet without pecan byproduct meal (Diet A) only experienced one day out of seventeen in which production was zero, namely, Day 11, after which egg production increased gradually back up to 50% by Day 17.

The results of Study 2 demonstrate that feed compositions having as little as about 3% by weight of pecan byproduct meal are effective for achieving the advantages of the present invention. It will be appreciated that even lower levels of pecan byproduct meal may be expected to yield positive results.

Through the above-identified studies, pecan byproduct meal has been demonstrated to significantly enhance the effectiveness of high fiber and low digestible carbohydrate diets for the rejuvenation of laying hens. Use of pecan byproduct meal effectively reduces calorie consumption, body weight, and egg production without resorting to the objectionable practice of extended feed withdrawal. Use of pecan byproduct meal in the feed permits hens to maintain intakes of vitamins, minerals, and other nutrients and to avoid the interruption of the normal functioning of the digestive tract experienced during prolonged fasting. Furthermore, and of particular importance, no mortality was associated with any of the regimens employed in the aforementioned studies. It is concluded that incorporation of pecan byproduct meal in the feed can effectively enable commercial egg producers to rejuvenate laying hen flocks without the extreme regimens objectionable to sectors of the general public.

Moreover, the use of pecan byproduct meal in the feed may assist in promoting the health of hens, in the same manner as conventional high fiber feeds.

While this invention has been described with reference to preferred embodiments thereof, it is to be understood that variations and modifications can be affected within the spirit and scope of the invention as described herein and as described in the appended claims.

We claim:

1. A chicken feed composition to promote health or rejuvenate egg production comprising:
    a. a feed suitable for consumption by chickens free of pecan byproduct meal; and
    b. a feed ingredient comprising a pecan byproduct meal composed of about 100% pecan packing tissue.

2. The feed composition of claim 1, wherein said feed suitable for consumption by chickens comprises a normal laying hen feed.

3. The feed composition of claim 1, wherein said feed suitable for consumption by chickens comprises a standard high fiber diet.

4. The feed composition of claim 1, further comprising a source of fiber comprising wheat middlings and soybean hulls.

5. The feed composition of claim 4, wherein said source of fiber constitute between 10% and 30% by total weight of said feed composition.

6. The feed composition of claim 1, wherein said pecan byproduct meal constitutes between about 3% and 15% by weight of said feed composition.

7. A chicken feed composition to promote health or rejuvenate egg production comprising:
    a. a feed suitable for consumption by chickens free of pecan byproduct meal; and
    b. a feed ingredient comprising a pecan byproduct meal composed primarily of pecan packing tissue essentially free of pecan shell and pecan meat, wherein said pecan byproduct meal constitutes at least about 3% by total weight of said feed composition.

8. The feed composition of claim 7, wherein said feed suitable for consumption by chickens comprises a standard high fiber diet.

9. The feed composition of claim 8, wherein fiber constitutes between 10% and 30% by total weight of said feed composition.

10. The feed composition of claim 8, wherein a source of fiber comprises wheat middlings and soybean hulls.

11. The feed composition of claim 7, wherein said feed suitable for consumption by chickens comprises a normal laying hen feed.

12. A method for feeding chickens to promote health or rejuvenate egg production comprising:
 a. feeding the chickens temporarily for between 2 and 17 days a feed comprising:
  i. a pecan byproduct meal composed primarily of pecan packing tissue essentially free of pecan shell and pecan meat until said chickens experience between approximately 18.1% and 23.2% reduction in body weight, whereby the chickens are induced to decrease egg production.

13. The method of claim 12, wherein said feed further comprises a standard high fiber diet.

14. The method of claim 12, wherein the total caloric intake of the chickens is limited to between 20 and 28 kilocalories per pound body weight per chicken.

15. The method of claim 12, wherein said feed further comprises a normal laying hen feed.

16. The method of claim 12, wherein the pecan byproduct meal constitutes at least about 3% by weight of the feed.

17. The method of claim 12, wherein the pecan byproduct meal constitutes between about 3% by weight of the feed and about 15% by weight of the feed.

18. The method of claim 12, wherein the feed further comprises a source of fiber.

19. The method of claim 18, wherein the source of fiber comprises wheat middlings and soybean hulls.

* * * * *